(12) United States Patent
Slatkine

(10) Patent No.: US 10,327,832 B2
(45) Date of Patent: *Jun. 25, 2019

(54) METHODS AND DEVICES FOR TISSUE ABLATION

(71) Applicant: Novoxel Ltd., Natania (IL)

(72) Inventor: Michael Slatkine, Herzlia (IL)

(73) Assignee: Novoxel Ltd., Natania (IL)

( * ) Notice: Subject to any disclaimer, the term of this patent is extended or adjusted under 35 U.S.C. 154(b) by 166 days.

This patent is subject to a terminal disclaimer.

(21) Appl. No.: 15/218,129

(22) Filed: Jul. 25, 2016

(65) Prior Publication Data

US 2016/0331440 A1    Nov. 17, 2016

Related U.S. Application Data

(62) Division of application No. 13/386,697, filed as application No. PCT/IL2010/000588 on Jul. 22, 2010, now Pat. No. 9,402,678.

(Continued)

(30) Foreign Application Priority Data

Jul. 27, 2009  (IL) .......................... 200081
Sep. 30, 2009  (IL) .......................... 201246

(51) Int. Cl.
*A61B 18/00* (2006.01)
*A61B 18/08* (2006.01)
*A61B 18/28* (2006.01)

(52) U.S. Cl.
CPC ............ *A61B 18/082* (2013.01); *A61B 18/08* (2013.01); *A61B 18/28* (2013.01);
(Continued)

(58) Field of Classification Search
CPC .................. A61B 18/08; A61B 18/082; A61B 2018/00625
(Continued)

(56) References Cited

U.S. PATENT DOCUMENTS 2,894,512 A    7/1959   Tapper
3,020,912 A    2/1962   Chester
(Continued)

FOREIGN PATENT DOCUMENTS

EP    1563788    8/2005
EP    1726329    11/2006
(Continued)

OTHER PUBLICATIONS

Supplementary European Search Report and the European Search Opinion dated Aug. 4, 2017 From the European Patent Office Re. Application No. 14871250.8. (7 Pages).

(Continued)

*Primary Examiner* — Christopher A Flory
(74) *Attorney, Agent, or Firm* — Brown Rudnick LLP

(57) ABSTRACT

A device for vaporizing a hole in tissue, including a vaporizing element, a heating element, configured to heat the vaporizing element, and a mechanism configured to advance the vaporizing element into a specific depth in the tissue and retract the vaporizing element from the tissue within a period of time long enough for the vaporizing element to vaporize the tissue and short enough to limit diffusion of heat beyond a predetermined collateral damage distance from the hole. Related apparatus and methods are also described.

18 Claims, 25 Drawing Sheets

Related U.S. Application Data

(60) Provisional application No. 61/326,667, filed on Apr. 22, 2010, provisional application No. 61/307,004, filed on Feb. 23, 2010.

(52) U.S. Cl.
CPC .............. *A61B 2018/0016* (2013.01); *A61B 2018/00095* (2013.01); *A61B 2018/00196* (2013.01); *A61B 2018/00577* (2013.01); *A61B 2018/00625* (2013.01); *A61B 2018/087* (2013.01)

(58) Field of Classification Search
USPC ............................................ 606/28; 607/89
See application file for complete search history.

(56) References Cited

U.S. PATENT DOCUMENTS

| | | | |
|---|---|---|---|
| 3,875,944 | A | 4/1975 | Toyama |
| 4,736,743 | A | 4/1988 | Daikuzono |
| 4,799,478 | A | 1/1989 | Fedorov et al. |
| 5,019,076 | A | 5/1991 | Yamanashi et al. |
| 5,064,426 | A | 11/1991 | Huebsch |
| 5,123,028 | A | 6/1992 | Hobart et al. |
| 5,318,562 | A | 6/1994 | Levy et al. |
| 5,360,447 | A | 11/1994 | Koop |
| 5,411,502 | A | 5/1995 | Zair |
| 5,423,803 | A | 6/1995 | Tankovich et al. |
| 5,498,258 | A | 3/1996 | Hakky et al. |
| 5,655,547 | A | 8/1997 | Karni |
| 5,733,278 | A | 3/1998 | Slatkine et al. |
| 5,885,211 | A | 3/1999 | Eppstein et al. |
| 5,899,915 | A | 5/1999 | Saadat |
| 5,908,419 | A | 6/1999 | Hahnen et al. |
| 6,142,939 | A | 11/2000 | Eppstein et al. |
| 6,296,639 | B1 | 10/2001 | Truckai et al. |
| 6,383,179 | B1 | 5/2002 | Neuberger |
| 6,475,138 | B1 | 11/2002 | Schechter et al. |
| 6,475,547 | B1 | 11/2002 | Lignell et al. |
| 6,530,915 | B1 | 3/2003 | Eppstein et al. |
| 6,678,556 | B1 | 1/2004 | Nolan et al. |
| 7,537,590 | B2 | 5/2009 | Santini et al. |
| 8,690,865 | B2 | 4/2014 | Prausnitz et al. |
| 8,808,311 | B2 | 8/2014 | Heinrich et al. |
| 8,834,461 | B2 | 9/2014 | Werneth et al. |
| 8,876,811 | B2 | 11/2014 | Lewinsky et al. |
| 2001/0020167 | A1 | 9/2001 | Woloszko et al. |
| 2002/0120260 | A1* | 8/2002 | Morris .............. A61B 18/1477 606/41 |
| 2002/0169394 | A1 | 11/2002 | Eppstein et al. |
| 2003/0092982 | A1 | 5/2003 | Eppstein |
| 2003/0097126 | A1 | 5/2003 | Woloszko et al. |
| 2003/0109802 | A1 | 6/2003 | Laeseke et al. |
| 2003/0212396 | A1 | 11/2003 | Eggers et al. |
| 2003/0216717 | A1 | 11/2003 | Nahen et al. |
| 2004/0181214 | A1 | 9/2004 | Garabedian et al. |
| 2004/0225286 | A1 | 11/2004 | Elliott |
| 2006/0024358 | A1 | 2/2006 | Santini et al. |
| 2006/0084942 | A1 | 4/2006 | Kim et al. |
| 2006/0095103 | A1 | 4/2006 | Eggers et al. |
| 2007/0149991 | A1 | 6/2007 | Mulholland |
| 2007/0167918 | A1 | 7/2007 | Reed et al. |
| 2007/0191827 | A1 | 8/2007 | Lischinsky et al. |
| 2008/0039832 | A1* | 2/2008 | Palanker .............. A61B 18/042 606/39 |
| 2008/0082090 | A1 | 4/2008 | Manstein |
| 2008/0091182 | A1 | 4/2008 | Mehta et al. |
| 2008/0091183 | A1 | 4/2008 | Knopp et al. |
| 2008/0091184 | A1 | 4/2008 | Knopp et al. |
| 2008/0091185 | A1 | 4/2008 | McGill et al. |
| 2008/0097558 | A1 | 4/2008 | Eggers et al. |
| 2008/0119761 | A1 | 5/2008 | Boecker et al. |
| 2008/0125775 | A1 | 5/2008 | Morris |
| 2008/0154254 | A1 | 6/2008 | Burger et al. |
| 2008/0200914 | A1 | 8/2008 | Hanlon et al. |
| 2008/0215039 | A1 | 9/2008 | Slatkine et al. |
| 2008/0281389 | A1 | 11/2008 | Knopp et al. |
| 2008/0312647 | A1 | 12/2008 | Knopp et al. |
| 2009/0036958 | A1* | 2/2009 | Mehta ............... A61B 18/1477 607/99 |
| 2009/0099534 | A1 | 4/2009 | Lee et al. |
| 2009/0112205 | A1* | 4/2009 | McGill .................. A61B 18/14 606/41 |
| 2009/0156958 | A1 | 6/2009 | Mehta et al. |
| 2009/0222000 | A1* | 9/2009 | Pacey ............... A61B 18/1477 606/33 |
| 2009/0234214 | A1 | 9/2009 | Santini et al. |
| 2009/0275899 | A1* | 11/2009 | Deem ................ A61K 41/0028 604/173 |
| 2009/0299361 | A1 | 12/2009 | Flyash et al. |
| 2009/0326571 | A1* | 12/2009 | Mulholland ......... A61B 17/205 606/186 |
| 2010/0010480 | A1 | 1/2010 | Mehta et al. |
| 2010/0081987 | A1 | 4/2010 | Christian |
| 2010/0121307 | A1 | 5/2010 | Lockard et al. |
| 2010/0217253 | A1 | 8/2010 | Mehta |
| 2010/0217254 | A1* | 8/2010 | Mehta .................... A61B 18/18 606/33 |
| 2010/0228243 | A1 | 9/2010 | Mehta |
| 2010/0262135 | A1 | 10/2010 | Berube |
| 2011/0028970 | A1 | 2/2011 | Woloszko et al. |
| 2011/0137386 | A1 | 6/2011 | Kreindel |
| 2011/0264084 | A1 | 10/2011 | Reid |
| 2011/0288543 | A1 | 11/2011 | Cheng et al. |
| 2012/0123401 | A1 | 5/2012 | Slatkine |
| 2012/0143178 | A9 | 6/2012 | Mehta |
| 2012/0158100 | A1 | 6/2012 | Schomacker |
| 2012/0185029 | A1 | 7/2012 | Flyash et al. |
| 2012/0330295 | A1 | 12/2012 | Manwaring et al. |
| 2013/0123767 | A1 | 5/2013 | Clark, III et al. |
| 2013/0184609 | A1 | 7/2013 | Lee et al. |
| 2013/0197473 | A1 | 8/2013 | McMillan |
| 2014/0171934 | A1 | 6/2014 | Flyash et al. |
| 2016/0317208 | A1 | 11/2016 | Slatkine et al. |
| 2017/0281256 | A1 | 10/2017 | Slatkine et al. |
| 2017/0281266 | A1 | 10/2017 | Slatkine et al. |

FOREIGN PATENT DOCUMENTS

| | | |
|---|---|---|
| EP | 1905516 | 4/2008 |
| EP | 2666424 | 11/2013 |
| FR | 2911059 | 7/2008 |
| JP | 03-063045 | 3/1991 |
| JP | 2006-192285 | 7/2006 |
| JP | 2007-531578 | 11/2007 |
| KR | 10-2009-0052631 | 5/2009 |
| KR | 10-0946363 | 3/2010 |
| WO | WO 91/10405 | 7/1991 |
| WO | WO 97/07734 | 3/1997 |
| WO | WO 2005/030071 | 4/2005 |
| WO | WO 2005/096979 | 10/2005 |
| WO | WO 2008/100118 | 8/2008 |
| WO | WO 2010/137885 | 12/2010 |
| WO | WO 2011/013118 | 2/2011 |
| WO | WO 2015/092791 | 6/2015 |
| WO | WO 2016/042546 | 3/2016 |
| WO | WO 2016/042547 | 3/2016 |

OTHER PUBLICATIONS

International Preliminary Report on Patentability dated Mar. 30, 2017 From the International Bureau of WIPO Re. Application No. PCT/IL2015/050924. (12 Pages).
International Preliminary Report on Patentability dated Mar. 30, 2017 From the International Bureau of WIPO Re. Application No. PCT/IL2015/050925. (10 Pages).
Communication Pursuant to Article 94(3) EPC dated Apr. 16, 2018 From the European Patent Office Re. Application No. 14871250.8. (8 Pages).
Applicant-Initiated Interview Summary dated Jul. 13, 2015 From the US Patent and Trademark Office Re. U.S. Appl. No. 13/386,697.

(56) References Cited

OTHER PUBLICATIONS

Communication Relating to the Results of the Partial International Search dated Dec. 3, 2010 From the International Searching Authority Re. Application No. PCT/IL2010/000588.
Communication Relating to the Results of the Partial International Search dated Feb. 5, 2016 From the International Searching Authority Re. Application No. PCT/IL2015/050924.
Examiner-Initiated Interview Summary and Advisory Action Before the Filing of an Appeal Brief dated Sep. 8, 2015 From the US Patent and Trademark Office Re. U.S. Appl. No. 13/386,697.
International Preliminary Report on Patentability dated Feb. 9, 2012 From the International Bureau of WIPO Re. Application No. PCT/IL2010/000588.
International Preliminary Report on Patentability dated Jun. 30, 2016 From the International Bureau of WIPO Re. Application No. PCT/IL2014/51103.
International Search Report and the Written Opinion dated Mar. 4, 2011 From the International Searching Authority Re. Application No. PCT/IL2010/000588.
International Search Report and the Written Opinion dated Jan. 8, 2016 From the International Searching Authority Re. Application No. PCT/IL2015/050925.
International Search Report and the Written Opinion dated Apr. 14, 2016 From the International Searching Authority Re. Application No. PCT/IL2015/050924.
International Search Report and the Written Opinion dated Jul. 22, 2015 From the International Searching Authority Re. Application No. PCT/IL2014/51103.
Invitation to Pay Additional Fees dated May 13, 2015 From the International Searching Authority Re. Application No. PCT/IL2014/051103.
Notice of Allowance dated Mar. 29, 2016 From the US Patent and Trademark Office Re. U.S. Appl. No. 13/386,697.
Notice of Reason for Rejection dated Apr. 4, 2014 From the Patent Office of Japan Re. Application No. 2012-522334 and Its Translation Into English.
Notice of Reason for Rejection dated Nov. 7, 2014 From the Patent Office of Japan Re. Application No. 2012-522334 and Its Translation Into English.
Office Action and Search Report dated Jul. 31, 2012 From the Israel Patent Office Re. Application No. 200081 and Its Translation Into English.
Office Action dated Feb. 2, 2014 From the Israel Patent Office Re. Application No. 217734 and Its Translation Into English.
Office Action dated Aug. 5, 2012 From the Israel Patent Office Re. Application No. 201246 and Its Translation Into English.
Office Action dated Dec. 14, 2014 From the Israel Patent Office Re. Application No. 217734.
Official Action dated Apr. 6, 2015 From the US Patent and Trademark Office Re. U.S. Appl. No. 13/386,697.
Official Action dated Nov. 6, 2014 From the US Patent and Trademark Office Re. U.S. Appl. No. 13/386,697.
Restriction Official Action dated Aug. 29, 2014 From the US Patent and Trademark Office Re. U.S. Appl. No. 13/386,697.
Translation Dated Jan. 15, 2015 of Office Action dated Dec. 14, 2014 From the Israel Patent Office Re. Application No. 217734.
Chernoff et al. "SilkTouch: A New Technology for Skin Resurfacing in Aesthetic Surgery", Journal of Clinical Laser Medicine & Surgery, 13(2): 97-100, 1995.
Dornier "Dornier Medials Fibertom 8100", Dornier MedTech, Product Sheet, 4 P., Feb. 2007.
Fee "Use of the Shaw Scalpel in Head and Neck Surgery", Otolaryngology—Head and Neck Surgery, 89(4): 515-519, Jul.-Aug. 1981.
Lowe et al. "Skin Resurfacing With the Ultrapulse Carbon Dioxide Laser. Observations on 100 Patients", Dermatologic Surgery, 21(12): 1025-1029, Dec. 1995.
Mestel "M3A10 Viscous Flow: Lubrication Theory—Flow in Thin Films", Graduate Course on Viscous Flow in Imperial College, London, UK, 4 P., 2013.
Park et al. "The Effect of Heat on Skin Permeability", International Journal of Pharmacology, 359(1-2): 94-103, Jul. 9, 2008.
PhotoMedex "Delivery Systems and Accessories for the SLT Contact Laser™ System", Surgical Laser Technology, PhotoMedex Inc., Catalog, 8 P., 2007.
Reed "Preventing Patient Thermal Burns From Electrosurgical Instruments", Reprint of Infection Control Today, 3 P., 2013.
Notification of Office Action dated Nov. 29, 2017 From the State Intellectual Property Office of the People's Republic of China Re. Application No. 201480074496.5 and Its Translation Into English. (9 Pages).
Communication Pursuant to Article 94(3) EPC dated Jun. 8, 2018 From the European Patent Office Re. Application No. 10747084.1. (5 Pages).
Restriction Official Action dated May 18, 2018 From the US Patent and Trademark Office Re. U.S. Appl. No. 15/105,086. (12 pages).
Non-Final Office Action dated Aug. 8, 2018 for U.S. Appl. No. 15/105,086 (20 Pages).

* cited by examiner

METHODS AND DEVICES FOR TISSUE ABLATION

RELATED APPLICATIONS

This application is a division of U.S. patent application Ser. No. 13/386,697 filed on Jan. 24, 2012, now U.S. Pat. No. 9,402,678, which is a National Phase of PCT Patent Application No. PCT/IL2010/000588 having International Filing Date of Jul. 22, 2010, which claims the benefit of priority of U.S. Provisional Patent Application Nos. 61/326,667 filed on Apr. 22, 2010 and 61/307,004 filed on Feb. 23, 2010, and claims priority from Israel Patent Application Nos. 201246 filed on Sep. 30, 2009 and 200081 filed on Jul. 27, 2009.

The contents of the above applications are all incorporated herein by reference as if fully set forth herein in their entirety.

FIELD AND BACKGROUND OF THE INVENTION

The present invention, in some embodiments thereof, relates to surgical methods and devices, and, more particularly, but not exclusively, to methods and devices for precise ablation of tissue.

The present invention opens up a wide variety of applications, some of which were historically implemented by use of a pulsed laser.

Pulsed $CO_2$ lasers are generally considered to be precise surgical tools for non-bleeding incision and ablation of tissue. Lasers such as the "Ultrapulse" $CO_2$ lasers are capable of char-free vaporizing a crater in tissue with collateral thermal damage of 50-100 microns. Such low collateral thermal damage is desired in applications such as neurosurgery, gynecology and aesthetic skin resurfacing, where scarring is undesirable. $CO_2$ lasers ablate or incise tissue by removing subsequent layers of tissue, each layer being approximately 30-50 microns deep, based on power and duration of the $CO_2$ laser pulse, and other considerations. $CO_2$ lasers are often used in a focused mode, with a focused beam of spot size of 50-300 microns.

For better understanding some embodiments of the present invention, as illustrated in FIGS. 2-17 of the drawings, reference is first made to FIG. 1 which is a simplified drawing of a prior art pulsed $CO_2$ laser 5 being used for ablation of tissue 10 by vaporization.

FIG. 1 depicts a simplified view of operating principles of a prior art, ablative, char-free, surgical, pulsed CO2 laser 5.

The $CO_2$ laser 5 is depicted in a first view at the top right of FIG. 1. The first view includes a $CO_2$ laser unit 6, an articulated arm 7 with an optic path or an optic fiber for directing a laser beam 17 from the $CO_2$ laser unit 6 to the tissue 10.

A second, enlarged, view at the left and bottom of FIG. 1 depicts an enlarged view of the beam 17 and a cross section of tissue 10.

The beam 17, the spot size of which may be 50-500 microns in diameter, is delivered from the pulsed $CO_2$ laser unit 6 to a surface of the tissue 10. The pulse duration is usually between 100 microseconds to 5 milliseconds. The optical beam 17 is absorbed by the tissue 10 down to a depth of approximately 30-50 microns. The absorbed optical beam 17 is transformed into thermal energy. The energy density of the optical beam 17 is typically selected to be above approximately 5 Joules/cm$^2$, which causes vaporization of the tissue 10 at a rate which exceeds the diffusion rate of heat into the tissue 10. As a result, a crater 15 is produced in the tissue 10, while the bulk of the tissue 10 which is vaporized is transformed into vapors 13, which are flushed. A collateral thermal damage zone 19 around the crater 15 is approximately from 50 to 150 microns deep, which is a diffusion depth of heat into the tissue 10 during a duration of a few milliseconds.

In a case where the tissue 10 is skin, FIG. 1 also depicts a layer 11 called papillary dermis. In a particular application of skin resurfacing, where an external surface of the skin is vaporized, it is usually desired to avoid any ablation of skin below a depth d of approximately 100-150 microns, which is the depth of the papillary dermis, in order to avoid scarring.

In other applications, such as very precise incisions, such as an eyelid incision, it is possible to drill deeper into the tissue, down to a tissue layer 14, by repeating the ablation of thin layers at the treatment site. Ablation of a surface of the skin, or of any tissue, by the $CO_2$ laser is typically performed by repeating the vaporization process described above with a scanner which moves the beam over the skin, or by using a large spot size beam. An example of large spot size beam can be a 10 mm diameter beam, which can still have an energy density above approximately 5 Joules/cm$^2$). Precise incisions are performed by a $CO_2$ laser by sequentially moving the beam in a linear or curved path.

U.S. Pat. No. 5,123,028 describes the Ultrapulse $CO_2$ laser, and U.S. Pat. No. 5,360,447 describes hair transplantation with the Ultrapulse $CO_2$ laser.

U.S. Pat. Nos. 5,411,502, 5,423,803 and 5,655,547 also describe $CO_2$ lasers for scar free incision and ablation of tissue with a focused beam. $CO_2$ laser beams can also be delivered to tissue through optical fibers. This is particularly useful for ablating tissue in minimal invasive procedures such as diskectomy Pulsed Erbium lasers operating at a wavelength of approximately 3 microns are also considered as superficial skin ablators. The pulsed Erbium lasers operate with large spot sizes (1-10 mm), and vaporize layers of approximately 10 microns of tissue. The pulse duration of erbium lasers is approximately 100-300 microseconds. Pulsed Erbium lasers are used as tools for professional peeling of skin when fast healing is desired (from a few hours to 1-2 days, and enabling patients to be back at work on the same day), due to a capability to operate above the papillary dermis without damaging the papillary dermis. In some countries performance of such peeling is allowed even by aestheticians, rather than physicians.

Additional background art also includes:
US Patent Application 2009/0156958 of Mehta et al;
US Patent Application 2009/0112205 of McGill et al;
US Patent Application 2009/0036958 of Mehta et al;
US Patent Application 2008/0312647 of Knopp et al;
US Patent Application 2008/0281389 of Knopp et al;
US Patent Application 2008/0091185 of McGill et al;
US Patent Application 2008/0091184 of Knopp et al;
US Patent Application 2008/0091183 of Knopp et al;
US Patent Application 2008/0091182 of Mehta et al;
US Patent Application 2007/0191827 of Lischinsky et al;
US Patent Application 2003/0109802 of Laeseke et al;
U.S. Pat. No. 6,475,138 to Schechter et al;
U.S. Pat. No. 6,296,639 to Truckai et al;
U.S. Pat. No. 5,733,278 to Slatkine et al;
An article on CO2 laser skin resurfacing by Chernoff G. et al, entitled "SilkTouch: a new technology for skin resurfacing in aesthetic surgery", published in J Clin Laser Med Surg. 1995 Apr.; 13(2):97-100;

An article by Lowe N J, et al, entitled "Skin resurfacing with the Ultrapulse carbon dioxide laser—Observations on 100 patients" published in Dermatol. Surg. 1995 Dec.; 21(12):1025-9;

A World Wide Web site for thermal conductivity coefficients of various metals: www(dot)engineeringtoolbox(dot)com/thermal-conductivity-metals-d_858 (dot)html; and A World Wide Web site for heat capacity of metals: www(dot)engineeringtoolbox(dot)com/specific-heat-metals-d_152(dot)html

SUMMARY OF THE INVENTION

The present invention, in some embodiments thereof, relates to surgical methods and devices, and, more particularly, but not exclusively, to methods and devices for precise ablation of tissue.

Prior art teaches using a laser to supply a large amount of heat, in a short amount of time, to ablate tissue.

The interaction between a char-free, minimal scarring, surgical laser beam and tissue is based on fast delivery of a large amount of heat to tissue—faster than the thermal relaxation time of the tissue, resulting in tissue vaporization rather than heat diffusion into the tissue The present invention, in some embodiments thereof, teaches using a vaporizing rod to supply a large amount of heat, in a short amount of time, to ablate tissue.

According to an aspect of some embodiments of the present invention there is provided a device for vaporizing a hole in tissue, including a vaporizing element, a heating element, configured to heat the vaporizing element, and a mechanism configured to advance the vaporizing element into a specific depth in the tissue and retract the vaporizing element from the tissue within a period of time long enough for the vaporizing element to vaporize the tissue and short enough to limit diffusion of heat beyond a predetermined collateral damage distance from the hole.

According to some embodiments of the invention, a tip of the vaporizing element has a shape designed for safety, so that the vaporizing element does not penetrate the tissue if the vaporizing element is not heated.

According to some embodiments of the invention, further including a battery as a power source.

According to some embodiments of the invention, the device is handheld.

According to some embodiments of the invention, the heating element is not in direct contact with the vaporizing element. According to some embodiments of the invention, the vaporizing element is in movement, the vaporizing element is not in contact with the heating element.

According to some embodiments of the invention, the vaporizing element is heated to a temperature in the range of 100 degrees Celsius to 800 degrees Celsius.

According to some embodiments of the invention, the vaporizing element is heated to a temperature such that a temperature differential T between the vaporizing element and the tissue, in degrees Celsius, is at least $T>(Hv*H)/(C \rho L)$, where Hv is a vaporization energy of a unit volume of the tissue, H is the specific depth, C is a heat capacity of the vaporizing element, and $\rho$ is a density of the vaporizing element.

According to some embodiments of the invention, the vaporizing element includes material having a thermal conduction coefficient greater than 80 watts per degree Kelvin per meter.

According to some embodiments of the invention, the vaporizing element includes material having a specific heat capacity greater than 0.3 kiloJoules per kilogram per degree Kelvin.

According to some embodiments of the invention, a length L of the vaporizing element is in the range $K T (Z/B)^2/(Hv H)>L>Hv*H/(C \rho T)$ where K is a coefficient of thermal conductivity of the vaporizing element, T is a temperature differential between the vaporizing element and the tissue, in degrees Celsius, Z is the predetermined collateral damage distance from the hole, B is a thermal diffusion coefficient in the tissue, Hv is a vaporization energy per unit volume of the tissue, H is the specific depth, C is a heat capacity of the vaporizing element, and $\rho$ is a density of the vaporizing element.

According to some embodiments of the invention, further including a plurality of vaporizing elements, and in which the mechanism is configured to advance and retract the plurality of vaporizing elements within a short period of time.

According to some embodiments of the invention, further including a spacer configured to limit the advance travel of the vaporizing element.

According to some embodiments of the invention, the device is placed within a package configured to be inserted into a body via a catheter.

According to some embodiments of the invention, the vaporizing element is detachable from the device.

According to some embodiments of the invention, further including a plurality of vaporizing elements, in which the mechanism is configured to advance and retract the plurality of vaporizing elements within a short period of time, and in which the spacer includes a plurality of holes through which the plurality of vaporizing elements can be driven into the tissue.

According to some embodiments of the invention, the spacer includes a hole through which the vaporizing element can be driven into the tissue.

According to some embodiments of the invention, further including a protective plate configured to be placed in contact with the tissue, and the vaporizing element is configured to extend the specific depth beyond the protective plate into the tissue.

According to some embodiments of the invention, the specific depth is in the range of 50 microns to 200 microns. According to some embodiments of the invention, the specific depth is adjustable.

According to some embodiments of the invention, the protective plate is flat within 30 microns along the full extent of the protective plate configured to be placed in contact with the tissue.

According to some embodiments of the invention, the protective plate configured to be placed in contact with the tissue includes a thermal insulator.

According to some embodiments of the invention the protective plate is detachable from the device.

According to some embodiments of the invention, the heating element includes a high temperature foil. According to some embodiments of the invention, the heating element includes an optical heat source.

According to some embodiments of the invention, the advancing and retracting are performed by one or more springs. According to some embodiments of the invention, the advancing and retracting are performed by a coil and a magnet.

According to some embodiments of the invention, the short period of time is determined by an oscillating period of a harmonic oscillator including the spring and the vaporizing element.

According to some embodiments of the invention, a rate of heating, advancing, and retracting supports repeated pulses of vaporization at a repetition rate of 1-100 pulses per second.

According to some embodiments of the invention, further including a harmonic oscillator, in which the harmonic oscillator includes the vaporizing element, and the harmonic oscillator has an oscillating period in the range from 10 milliseconds to 100 milliseconds. According to some embodiments of the invention, further including a mechanism to limit oscillation of the harmonic oscillator to a single oscillation.

According to some embodiments of the invention, the heating element is configured to heat the vaporizing element to a temperature above vaporization temperature of the tissue. According to some embodiments of the invention, the heating element is configured to heat the vaporizing element to a temperature in a range from 200 to 600 degrees Celsius.

According to some embodiments of the invention, the vaporizing element includes a material with heat conductivity equal to or higher than heat conductivity of copper. According to some embodiments of the invention, the vaporizing element includes a material with specific heat capacity equal to or higher than specific heat capacity of copper.

According to some embodiments of the invention, a length of the vaporizing element is between 0.3 mm and 5 mm.

According to some embodiments of the invention, the vaporizing element is shaped so as not to substantially penetrate the tissue when the heated to a temperature substantially less than a vaporization temperature of the tissue.

According to some embodiments of the invention, a combination of a temperature to which the vaporizing element is heated and a duration of the short time are selected so as to limit collateral damage to the tissue to a distance of less than 150 microns.

According to some embodiments of the invention, the short time is less than a thermal relaxation time in tissue for a distance of 150 micron. According to some embodiments of the invention, the short time is less than 5 milliseconds.

According to an aspect of some embodiments of the present invention there is provided a method for vaporizing a hole in tissue, including heating a vaporizing element, and using a mechanical device to advance the vaporizing element to a desired depth within the tissue and retract the vaporizing element from the tissue after a short duration.

According to some embodiments of the invention, in order to produce the hole having a depth of H in the tissue, and having collateral damage extend a distance of no more than Z from the hole, in tissue having a thermal diffusion coefficient B and a vaporization energy per unit volume Hv, using a temperature differential between the vaporizing element and the tissue, in degrees Celsius, of T, using a vaporizing element such that $K C \rho > (Hv H B)^2/(T Z)^2$ where K is a coefficient of thermal conductivity of the vaporizing element, C is a heat capacity of the vaporizing element, and $\rho$ is a density of the vaporizing element.

According to some embodiments of the invention, further including heating a plurality of vaporizing elements, and using the mechanical device to advance the plurality of elements to a desired depth within the tissue and retract the elements from the tissue after a short duration.

According to an aspect of some embodiments of the present invention there is provided a method of causing live skin to tighten including with a device including a plurality of vaporizing elements, heating the vaporizing elements, and using the device to advance the plurality of vaporizing elements to a depth which is smaller or equal to a papillary dermis depth within the live skin, and retract the vaporizing elements from the live skin after a short duration, producing a plurality of craters in the skin, inducing the live skin to tighten.

According to an aspect of some embodiments of the present invention there is provided a method of ablating tissue for one of the group of uses including neurosurgery, orthopedics, ear surgery, nose surgery, throat surgery, gynecology, dermatology, and dentistry, including heating a vaporizing element, and using a mechanical device to advance the vaporizing element to a desired depth within the tissue and retract the vaporizing element from the tissue after a short duration.

According to an aspect of some embodiments of the present invention there is provided a method of material incision including heating a vaporizing element, using a device to advance the vaporizing element to a depth which is smaller or equal to a papillary dermis depth within the skin, and retract the vaporizing element from the skin after a short duration, generating a crater in the skin, and repeating the heating, the advancing, and the retracting, while moving the device along a course of the incision.

According to some embodiments of the invention, the material includes live tissue.

According to an aspect of some embodiments of the present invention there is provided a vaporizing element for vaporizing a hole in tissue, including one or more tips with a shape designed for safety, so that the vaporizing element does not penetrate the tissue if the vaporizing element is not heated.

According to some embodiments of the invention, the vaporizing element includes material having a thermal conduction coefficient greater than 80 watts per degree Kelvin per meter.

According to some embodiments of the invention, the vaporizing element includes material having a specific heat capacity greater than 0.3 kiloJoules per kilogram per degree Kelvin.

According to some embodiments of the invention, a length L of the vaporizing element is in the range $$KT(Z/B)^2/(HvH) > L > Hv*H/(C\rho T)$$

Where K is a coefficient of thermal conductivity of the vaporizing element, T is a temperature differential between the vaporizing element and the tissue, in degrees Celsius, Z is the predetermined collateral damage distance from the hole, B is a thermal diffusion coefficient in the tissue, Hv is a vaporization energy per unit volume of the tissue, H is the specific depth, C is a heat capacity of the vaporizing element; and $\rho$ is a density of the vaporizing element.

According to some embodiments of the invention, a ratio of a total distal end area of the tips to a total area of gaps between the tips is between 5% and 80%.

According to an aspect of some embodiments of the present invention there is provided a protective plate configured to be placed in contact with tissue, including holes sized so as to allow a vaporizing element to pass therethrough and extend a specific depth beyond the protective plate into the tissue.

According to some embodiments of the invention, the protective plate is flat within 30 microns along the full extent configured to be placed in contact with the tissue.

According to some embodiments of the invention, the protective plate comprises a thermal insulator.

According to some embodiments of the invention, further including a cooling means for cooling the protective plate.

According to an aspect of some embodiments of the present invention there is provided a kit including a vaporizing element for vaporizing a hole in tissue, including one or more tips with a shape designed for safety, so that the vaporizing element does not penetrate the tissue if the vaporizing element is not heated, and a protective plate configured to be placed in contact with the tissue, including holes sized so as to allow the one or more tips of the vaporizing element to pass therethrough and extend a specific depth beyond the protective plate into the tissue.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
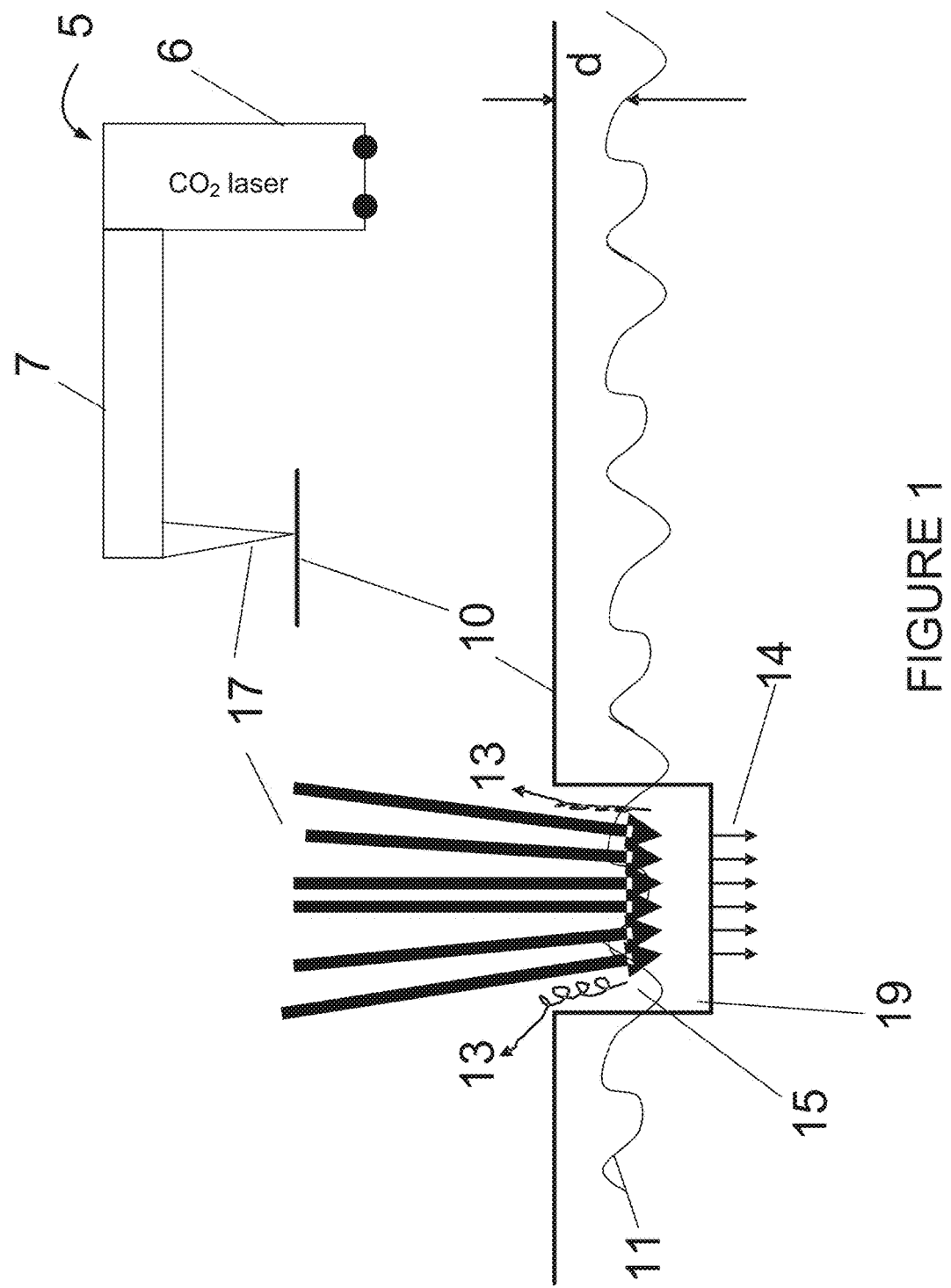
FIG. 1 is a simplified drawing of a prior art pulsed CO2 laser being used for ablation of tissue by vaporization.

The present invention, in some embodiments thereof, relates to surgical methods and devices, and, more particularly, but not exclusively, to methods and devices for precise ablation of tissue.

The present invention, in some embodiments thereof, teaches using a vaporizing rod to supply a large amount of heat, in a short amount of time, to ablate tissue. The vaporizing rod is able to supply a large amount of heat, in a short amount of time, to vaporize and ablate the tissue.

In order to vaporize tissue which is to be vaporized, while not destroying tissue which should not be destroyed, the present invention, in some embodiments thereof, teaches applying heat at a high temperature to a localized area in tissue.

The temperature should be high enough to rapidly vaporize the tissue, that is, a temperature above 100 degrees Celsius, which is a boiling temperature of water, which is a major constituent of tissue.

Preferably, the temperature should be higher than approximately 200 degrees Celsius.

The heat capacity of the vaporizing rod should be such that a tip of the vaporizing rod which is adjacent to the tissue contains an amount of heat which is enough to vaporize the tissue which is adjacent to the tip. The amount of heat necessary to vaporize tissue is dependent on the volume to be vaporized. The volume to be vaporized approximately equals a cross section of the tip, multiplied by the depth which is to be vaporized.

By way of a non-limiting example, in order to vaporize an area of 100 microns by 100 microns, to a depth of 100 microns, approximately 3 milliJoules of heat are needed, based on the vaporization energy of water which is approximately 3,000 Joule/cm$^3$. It is noted that the heat needed to vaporize tissue is substantially close to the heat needed to vaporize water, since tissue thermal parameters are very similar to water thermal parameters.

In order to supply the heat to the tissue, the heat relaxation time of the vaporizing rod, should be such that the heat can come rapidly to the surface of the tip of the vaporizing rod.

It is noted that the heat relaxation time depends, among other factors, on heat conductivity, heat capacity, and geometric dimensions, such as length, of the vaporizing rod.

The heat supply should be fast enough to vaporize the adjacent tissue without allowing too much heat to diffuse into the tissue, that is, a heat relaxation time substantially shorter than that which produces an allowed or planned necrosis depth in tissue. By way of approximation, the heat relaxation time should be substantially shorter than that of water.

In some embodiments, the vaporizing rod is "flicked" onto the tissue for a very short and limited amount of time. The flicking keeps the vaporizing rod adjacent, optionally in contact, to the tissue for only a short time, limiting time for heat conductance into tissue, and limiting collateral damage to acceptable levels.

In some embodiments of the invention a distance of collateral damage is calculated as a heat diffusion coefficient of the tissue, multiplied by a square root of a time the source of the heat, that is, the vaporizing rod, provides heat to the tissue.

In some embodiments of the invention the vaporizing rod is considered as providing heat to the tissue as long as the vaporizing rod is adjacent to the tissue.

In some embodiments of the invention the vaporizing rod is considered as providing heat to the tissue as long as the vaporizing rod is within the volume of the crater.

In some embodiments there is more collateral damage allowed then in others. By way of a non-limiting example, In applications involving live tissue areas rich in blood vessels, a little collateral damage may be good, for cauterizing the blood vessels. In applications involving live tissue areas not rich in blood vessels, less collateral damage may be desirable. In applications involving non-live tissue, more or less collateral damage may also be a consideration.

In some embodiments, the vaporizing rod is prevented from over-travel by an over-travel guard.

In some embodiments, the vaporizing rod is prevented from touching the tissue when not being "flicked" onto the tissue, by a tissue guard which keeps the vaporizing rod from touching tissue except when "flicked" beyond the guard onto the tissue.

In some embodiments, typical dimensions of rods are from 100 microns to 5 millimeters in width, from 2 millimeters to 10 millimeters long, depending on application.

Some embodiments of the invention use an array of a plurality of vaporizing rods. The rods are optionally arranged in arrays, either linear or two dimensional, also depending on application.

Typical movement lengths of the rods are from 1 to 10 millimeters, while typically advancing from 50 microns to 500 microns into tissue, in the vaporizing phase.

Typical durations of movement are such that the dwell time of the vaporizing rod(s) in tissue during the vaporization phase are from 100 microseconds to 50 milliseconds, depending on application.

The use of the term rod herein as part of "vaporizing rod" is not meant to imply a shape of a rod, and is intended to mean "vaporizing element".

In some embodiments a shape, or geometry, of a cross section of a tip of the vaporizing rod which performs the vaporizing of tissue, is a solid circle, a solid rectangle, a hollow circle, a hollow rectangle, a straight line, a curve, a wavy line, and various other "cookie cutter" shapes, depending on application.

Some embodiments of the invention use a metal rod for the vaporizing. Metal can contain and/or conduct enough heat for vaporization, and can be shaped with a great degree of accuracy.

Some embodiments of the invention include more than one vaporizing rod, and ablate tissue simultaneously using the more than one vaporizing rod.

In some embodiments of the invention the vaporizing rod is heated by an electric heating element.

In some embodiments of the invention the vaporizing rod is heated by a wireless heating method such as optical heating by light waves, or heating by microwaves.

In some embodiments of the invention the tissue is cooled after retraction of the vaporizing rod. The cooling is optionally performed by blowing air, and/or by blowing a liquid mist and/or by spraying liquid and/or by a thermoelectric chiller, and/or by placing a cold metallic plate on the tissue, and/or by a protective plate through which the vaporizing rod passes being adapted to cool the tissue, by conducting heat away from the tissue and/or by active cooling. Active cooling may be a liquid cooler cooling the protective plate, by a gas flowing and cooling the protective plate, or by thermocouple cooling the electric plate.

Is some embodiments, where there is repeated application of the vaporizing rod to the tissue, the cooling is performed between every application of the vaporizing rod. In some applications the cooling is performed after a last application of the vaporizing rod.

In some embodiments of the invention the heating element is connected to a power supply by an electric power line, enabling separation of the power supply from the heating element. In some embodiments of the invention the electric heating element and the vaporizing rod are small enough to be inserted into a body. In some embodiments, the electric heating element and the vaporizing rod are small enough even for insertion by a catheter.

In some embodiments of the invention the vaporizing rod is electrically insulated from the tissue, so as not to produce an electrical contact with the tissue being ablated.

In some embodiments of the invention the vaporizing rod is electrically insulated from the electric power supply, also so as not to produce an electrical contact with the tissue being ablated.

Some embodiments of the invention include a mechanical travel limiter, such that the vaporizing rod cannot travel more than a specified distance beyond the mechanical travel limiter. The mechanical travel limiter optionally rests in contact with tissue, and the vaporizing rod is limited from travelling more than the specified distance beyond the mechanical travel limiter, limiting the depth which the vaporizing rod can ablate the tissue.

The mechanical travel limiter is optionally simple to manufacture and fail-safe, providing an advantage over some laser ablation limiters which limit an amount of time during which a laser beam is applied to the tissue. The advantage is in cost and/or safety and/or reliability.

Some embodiments of the invention are designed to be small—much smaller than a typical medical $CO_2$ laser, and some embodiments are designed to be small enough to be inserted into a body, even inserted by a catheter. In some embodiments the heating element is connected to a power supply by a flexible electric wire, which enables the ablator to be inserted into the body with a flexible catheter and a flexible wire. CO2 lasers sometimes use fiber optics to conduct the laser pulse, but at a much higher cost than that of an electric wire.

In some embodiments of the invention, using a single vaporizing rod with a diameter of 300 microns, it is possible to use catheters with a diameter of approximately 2 millimeters.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Figure 2:
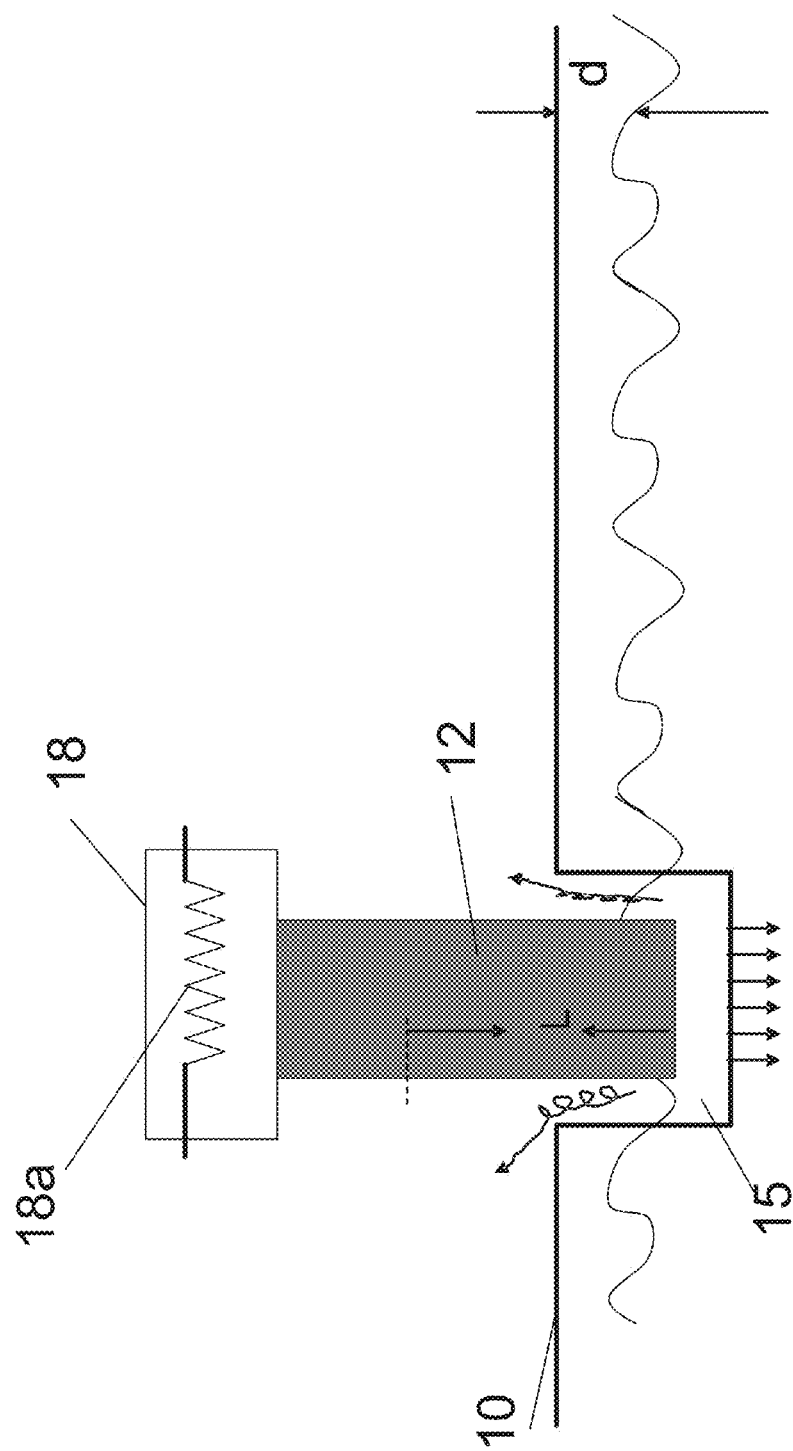
FIG. 2 is a simplified drawing of an embodiment of the present invention being used for ablation of tissue by vaporization.

Reference is now made to FIG. 2, which is a simplified drawing of an embodiment of the present invention being used for ablation of tissue 10 by vaporization.

FIG. 2 depicts an example operation of an embodiment of the current invention being used, by way of a no-limiting example, for the same effect as the $CO_2$ laser of FIG. 1.

The embodiment of the present invention, as depicted in FIG. 2, includes a vaporizing rod 12, heated to a temperature much higher than the boiling point of tissue.

The rod 12 is optionally heated via a foil 18, which is optionally heated by an electrical resistor 18a.

Figure 12:
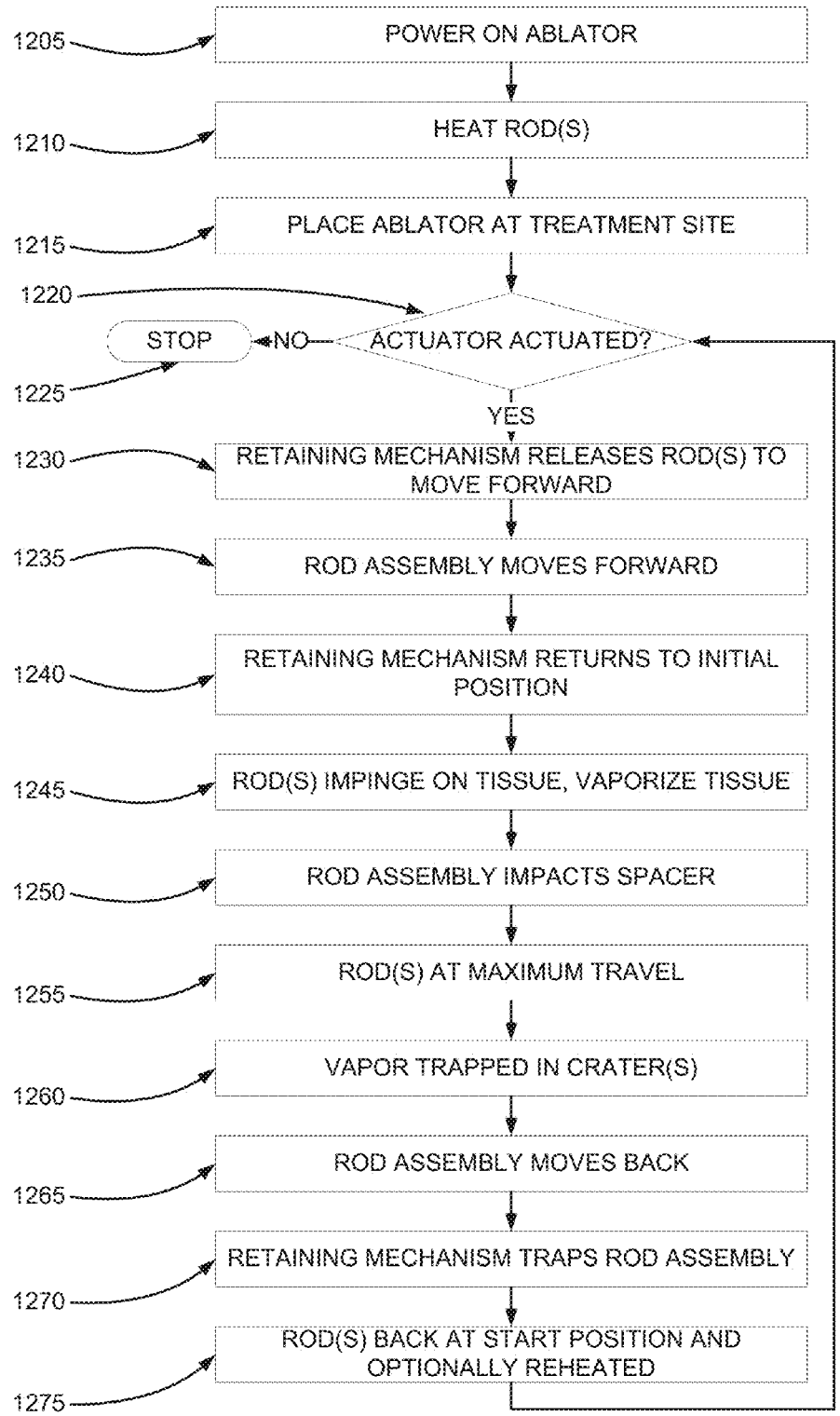
FIG. 12 is a simplified flow chart illustrating a method of using an embodiment of the present invention as a tissue ablator.

Some measurements involving the example embodiment of FIG. 12, include the vaporizing rod 12 having a diameter of 300 microns, and made, by way of a non-limiting example, of copper. The rod 12 is heated, by way of a non-limiting example, to a temperature of approximately 200 to 600 degrees Celsius. In some embodiments the vaporizing rod is heated to a temperature of approximately 400 degrees Celsius, so carbon particles which may reside on walls of a vaporized crater get oxidized and transformed into $CO_2$ vapors at a temperature of approximately 400 degrees Celsius, resulting in char-free crater walls. Char-free crater walls further promote healing.

The rod 12 is optionally heated via a Mica foil 18.

Additional means to heat the rod 12 to a required temperature are described below, with reference to FIG. 9.

The rod 12 is advanced into tissue 10 down to a preselected depth H, optionally between 50 and 200 microns, and retracted. Examples of advancing mechanisms, as well as ways to ensure control of advance into tissue are described below. Advance and retraction speeds are optionally selected to determine a dwell time of the rod 12 distal end in tissue.

In some cases, a dwell time of approximately 100 microseconds to approximately 5 milliseconds is selected.

In some cases the dwell time is extended to 100 milliseconds to allow more of a cauterizing action.

In some cases the dwell time is approximately 100 microseconds, to produce as little as possible collateral damage. A short dwell time, such as 100 microseconds, may in some cases not be long enough to avoid bleeding, as often occurs with Erbium lasers. A dwell time of approximately 1 to 5 milliseconds is considered optimal for producing collateral thermal necrosis ranging in depth from 100 microns to 150 microns, which ensures, for example, sparing the papilla dermis and avoiding scaring.

In some case a longer dwell time, such as from 50 milliseconds to 100 milliseconds, is allowed, and even advantageous. The longer dwell time is advantageous in cases such as, by way of a non-limiting example, myringotomy, where delayed healing is advantageous. For example, in myringotomy, delayed healing is considered advantageous in order to leave the tympanic membrane ventilated without insertion of tubes.

In some case an even longer dwell time is allowed. The vaporizing rod is advanced into tissue, and left within the tissue. The vaporizing rod vaporizes tissue until cooling off so much that remaining heat in the vaporizing rod does not adversely affect the tissue.

In some embodiments of the invention penetration of the rod 12 into the tissue 10 is optionally enabled only due to vaporization of the tissue 10 and creation of a crater 15. The speed of the rod 12 while in contact with the tissue 10 is optionally low enough so as not to penetrate tissue if the rod 12 is not heated to the vaporization temperature of the tissue 10, unlike, for example, an injection needle.

Vaporizing thermal energy is delivered to the tissue 10, in the embodiment depicted in FIG. 2, for the same time duration as in the case of the $CO_2$ laser of FIG. 1. Substantially the same tissue vaporization effect is achieved, including a substantially identical collateral thermal damage.

It is noted that by selecting thermal parameters, such as on or more of temperature, heating rate, vaporizing rod material, the embodiment of FIG. 2 can work and mimic operation of an Ultrapulse and/or Superpulse $CO_2$ laser beam.

By way of a non-limiting example, the $CO_2$ laser of FIG. 1 has a focal spot size of 300 microns, and enables high precision incisions and ablation. The example embodiment of FIG. 2 can achieve the same performance.

It is noted that in order to achieve minimal thermal damage of approximately 50-150 microns around the vaporized crater 15, it is desired to deliver thermal energy within approximately 5 milliseconds or less. The energy necessary to vaporize a 300×300 micron area, 100 micron depth, crater 15 is approximately 30 milliJoules, based on the vaporization energy of water which is approximately 3000 Joule/$cm^3$. It is noted that tissue thermal parameters are very similar to water thermal parameters. In the embodiment of FIG. 2, the vaporizing energy originates from thermal energy in the distal end L of the rod 12. The thermal energy in distal end L of the rod 12 depends on the heat capacity, size, and shape of distal end L of the rod 12.

Heat Capacity and Heat Conductivity

Based on heat capacities of metals, it can be shown that in order to store and deliver approximately 30 milliJoules from a metallic rod with a diameter of 300 microns at approximately 400 deg C. to the tissue 10, the energy should flow from a rod distal section of a length L typically in a range of approximately 300 microns to 5000 microns. However, the thermal conductivity of many metals such as stainless steel is too low to allow flow of the necessary energy (30 milliJoules) from a distance as described above, and having a cross section as described above, to a tissue at approximately 100 degrees Celsius during approximately 5 milliseconds.

Some materials, such as some metals, have thermal conductivity as high as, by way of a non-limiting example, copper, enable such rapid heat flow. A heated rod which mimics an Ultrapulse and/or a Superpulse $CO_2$ laser may optionally be made of copper, should optionally be heated to a temperature of approximately 300-500 degrees Celsius, and should be advanced into tissue at a speed which optionally produces a dwell time in tissue of approximately 5 milliseconds, and to a depth of approximately 50-200 microns.

It is noted that carbon particles which may be present on the walls of the vaporized are oxidized at a temperature of approximately 400 deg C. and discarded as carbon dioxide vapors, resulting in an advantage of heating the rod to a temperature above 400 deg C.

In some example embodiments of the invention the following example estimations are used for selecting properties of a vaporizing rod or rods to supply a large amount of heat, in a short amount of time, to ablate tissue. The example estimations teach how to choose proper materials, temperatures, and dimensions for the vaporizing rod or rods in the example embodiments, in order to produce a desired hole in tissue, with a selected amount of collateral heat damage.

The energy Ev needed to vaporize a crater with, for example, a square shape of width d and a depth H is:

$$Ev = Hv * d^2 * H; \qquad \text{Equation 1}$$

where Hv is a vaporization energy of 1 cubic centimeter of tissue (approximately 3000 Joules/cm$^3$).

A rate of heat flow W from a square rod of length L, width d, thermal conductivity K, and a temperature T higher than a temperature of the tissue is approximately:

$$W = KTd^2 1L; \qquad \text{Equation 2}$$

The heat flow enables a flow of energy E into tissue within a time duration t, where E=W*t.

Thermal heat E which is stored in the rod and may be available for vaporizing tissue is given by:

$$E = C * \rho * L * d^2 * T \qquad \text{Equation 3}$$

where C=heat capacity, ρ=vaporizing rod material density.

The extent (distance) Z of collateral thermal damage in tissue, for a vaporization time t, is given by $$Z = B\sqrt{t}; \qquad \text{Equation 4}$$

where B is a thermal diffusion coefficient in tissue.

The following equations describe conditions for tissue to vaporize producing a crater having collateral thermal damage of depth Z:

$$t = (Z/B)^2 \qquad \text{Equation 5}$$

$$E = C\rho Ld^2 T > Ev = Hv * d^2 * H \qquad \text{Equation 6}$$

or $$L > Hv * H/(C\tau T) \qquad \text{Equation 7}$$

Equation 7 determines a lower limit to the length of the vaporizing rod.

From equations 1, 2, and 4 the following is determined:

$$tKTd^2/L > Ev = Hvd^2 H; \qquad \text{Equation 8}$$

or $$L < KT(Z/B)^2/(HvH); \qquad \text{Equation 9}$$

Equation 9 sets an upper limit to the length L of the vaporizing rod.

By using equations 7 and 9, it is possible to select parameters for the vaporizing rods according to the current invention.

For example, the length L of the vaporizing rod is preferably in the range:

$$KT(Z/B)^2/(HvH) > L > Hv * H/(C\tau T) \qquad \text{Equation 10}$$

For example, the temperature differential T between the vaporizing rod and the tissue, in degrees Celsius, is preferably in the range:

$$T > (Hv * H)/(C\rho L) \qquad \text{Equation 11}$$

It is noted that when designing a vaporizing rod, the temperature differential T is a parameter which is taken into account, together with other reasonable parameters, such as that the temperature of the vaporizing rod is not above a melting point of the rod material, that the temperature of the vaporizing rod does not make the rod material break down in some way, and that the length L of the vaporizing rod optionally preserves the constraint of Equation 10.

For example, in order to produce the hole having a depth of H in the tissue, and having collateral damage extend a distance of no more than Z from the hole, in tissue having a thermal diffusion coefficient B and a vaporization energy per unit volume Hv, using a temperature differential between the vaporizing rod and the tissue, in degrees Celsius, of T, selecting the vaporizing rod to have thermal parameters K C ρ such that:

$$KC\rho > (HvHB)^2/(TZ)^2 \qquad \text{Equation 12}$$

It is noted that setting a temperature differential T between the vaporizing element and the tissue, is typically determined by two constraints: a desire for vaporizing tissue and avoiding charring of the tissue. The two constraints determine the temperature differential T to be approximately 400 degrees Celsius.

By way of a non-limiting example, for a specific case of skin vaporization down to the papillary dermis, with collateral damage depth of 100 to 150 microns, which entails a dwell time duration of 1 to 5 milliseconds, is limited to a length of L ~650 microns, when using copper as a material from which the vaporizing rod is produced, and T ~400 degrees Celsius.

It is noted that in some cases, the vaporization depth is kept at approximately 40 microns into the tissue, and thermal damage is kept at approximately 40 microns, enabling a peeling of substantially only epidermis, without affecting the papillary dermis, similarly to what cosmetologists do when superficially peeling skin. In such cases, the dwell time duration may be approximately 250 microseconds, the temperature of the vaporizing rod may be in the range from 300 to 500 degrees Celsius, and the vaporizing rod length may be approximately in the range 200 to 300 microns. The rod may optionally be produced from a high thermal conductivity non-metallic material such as, byway of a non-limiting example, artificial diamond.

It is noted that the depth of the crater which is vaporized by the vaporizing rod is not necessarily identical to the penetration depth of the rod. Heat is diffused from the rod into the tissue, and vaporizes the tissue ahead of the vaporizing rod. However, the equations above provide may be used guidelines for a selection of vaporizing rod parameters.

In some applications, such as removal of a fatty layer around an organ, the thermal properties of the fatty layer to be removed may vary from those of a water-rich tissue. However, the equations above provide a guideline for the selection of the physical parameters of the vaporizing rods, taking into account appropriate values for Hv, the vaporization energy of tissue and B, the thermal diffusion coefficient in the tissue.

In some embodiments of the invention, the vaporizing rod is made of a combination of two metals. For example, a copper rod is coated with a thin layer, approximately 5 microns thick, of a considerably less heat conductive metal such as stainless steel. The stainless steel is useful for biocompatibility.

In some embodiments of the invention, the vaporizing element is not a solid rod, but a heated fluid, which is forcibly sprayed at the tissue, at a temperature which can vaporize tissue. After spraying the heated fluid, a cooling fluid is optionally sprayed. The heated fluid may optionally be a body-safe silicone fluid.

In some embodiment of the invention, the vaporizing rods are hollow, and incorporate a small amount, such as approximately 0.1 milligrams to 5 milligrams of chemical reactants, which optionally react in an exothermic reaction which produces the heat necessary for elevating the temperature of the vaporizing rods. Such an approach is optionally used in cases when the vaporizing rod is heated once before being recharged with reactants or discarded. One such example use is in case of myringotomy, as further described below with reference to example application 8.

The exothermic reaction may be, by way of a non-limiting example, between oxidized iron and aluminum, also termed the "thermite" reaction. In some embodiments the reactants are optionally activated by electricity. In some embodiments the reactants are optionally pre-heated to a temperature below ignition while the vaporizing rod is away from the tissue, and ignited, optionally be electricity, when the vaporizing rod advances toward the tissue.

The thermite reaction generates a very high temperature—over 1500 degrees Celsius. The hollow rod is optionally produced from a material with a higher melting temperature than the reaction temperature, such as, by way of a non-limiting example, Titanium. The heat of the reaction flows into the tissue and vaporizes the tissue. The vaporizing rod is optionally produced with an inner diameter in the range of approximately 200 microns to 800 microns, and with a greater outer diameter in the range of approximately 300 microns to 900 microns.

Figure 3:
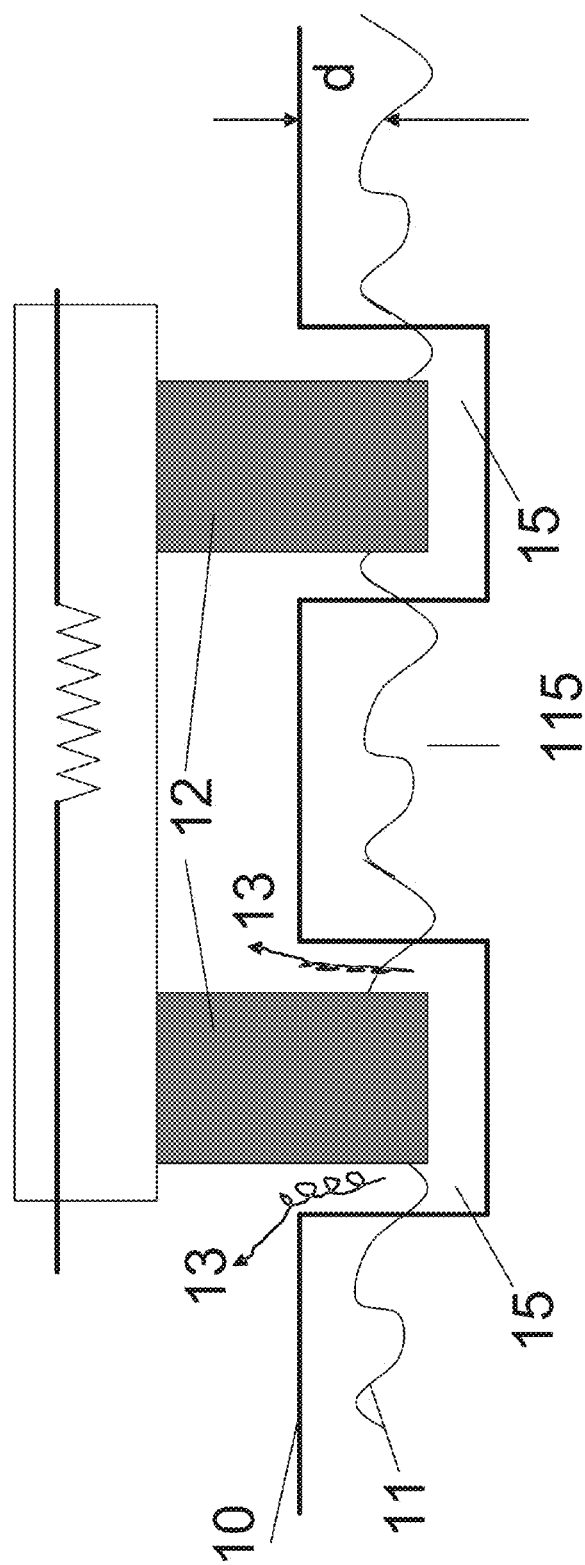
FIG. 3 is a simplified drawing of another embodiment of the present invention, having two vaporizing rods, being used for ablation of tissue by vaporization.

Reference is now made to FIG. 3, which is a simplified drawing of another embodiment of the present invention, having two vaporizing rods, being used for ablation of tissue by vaporization.

FIG. 3 depicts an embodiment of the present invention in which more than one rod 12 are simultaneously advanced into tissue 10. The rods 12 of FIG. 3 are optionally separated, so when advanced into the tissue 10, two of craters 15 are produced.

For some implementations, such as skin resurfacing, a multitude of craters are desired. The embodiment of FIG. 3 is an example of two vaporizing rods, and teaches that a plurality of vaporizing rods can be used.

In some embodiments of the invention the plurality of vaporizing rods are arranged as an array of vaporizing rods.

Figure 4A:
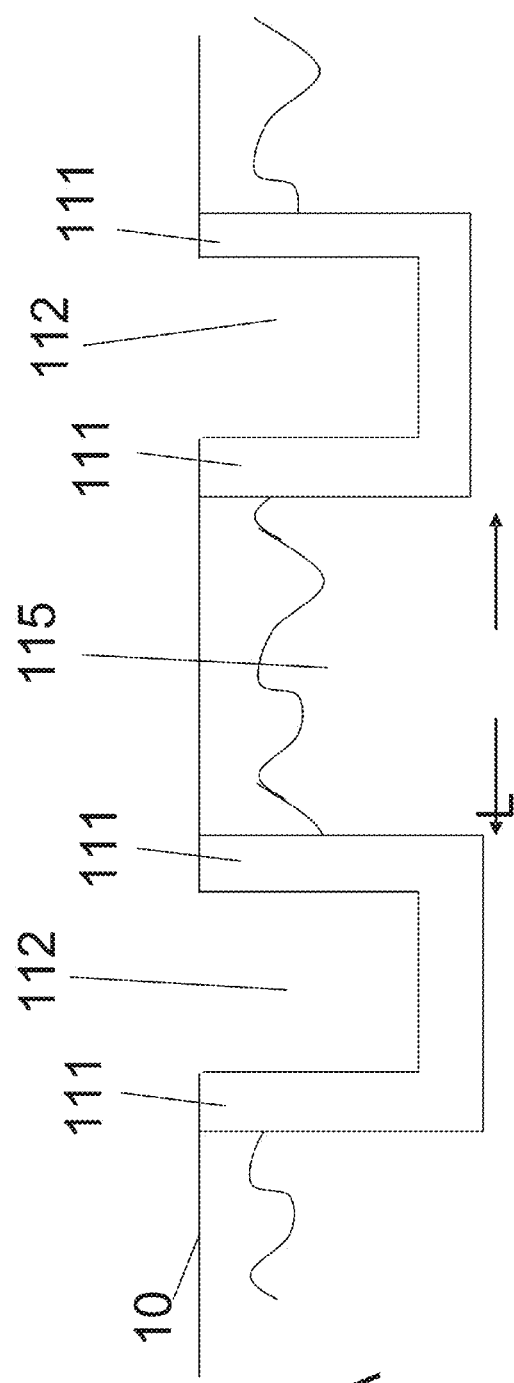
FIG. 4A is a simplified cross-sectional drawing of an array of char-free craters drilled in tissue by yet another embodiment of the present invention, having an array of vaporizing rods.

Reference is now made to FIG. 4A, which is a simplified cross-sectional drawing of an array of char-free craters drilled in tissue by yet another embodiment of the present invention, having an array of vaporizing rods.

FIG. 4A depicts a cross section of tissue 10 with two craters 112, each with a collateral thermal damage zone 111 of width in the range, by way of a non-limiting example, from 50 to 150 microns, and a healthy, untreated section 115 of length L.

Such a configuration may be used for skin resurfacing by a technique termed Fraxel. The Fraxel technique enables the untreated section 115 to grow into the treated sections. The Fraxel technique enables accelerate healing of the tissue 10.

Figure 4B:
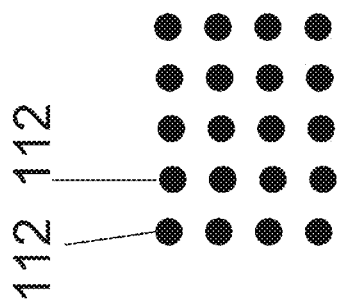
FIG. 4B is a simplified top-view drawing of an array of char-free craters drilled in tissue by yet another embodiment of the present invention, having an array of vaporizing rods.

Reference is now made to FIG. 4B, which is a simplified top-view drawing of an array of char-free craters drilled in tissue by yet another embodiment of the present invention, having an array of vaporizing rods.

FIG. 4B depicts an array of 4×5 craters, by way of a non-limiting example having a diameter of 300 microns, separated by a distance of 700 microns. The array of craters can be generated by using a 20 rod array. By way of another example, arrays of 10×10 arrays should also be conveniently used in Fraxel skin resurfacing.

By way of a non-limiting example the craters 110 112 which are depicted in FIG. 4A are also referenced in FIG. 4B.

Figure 5:
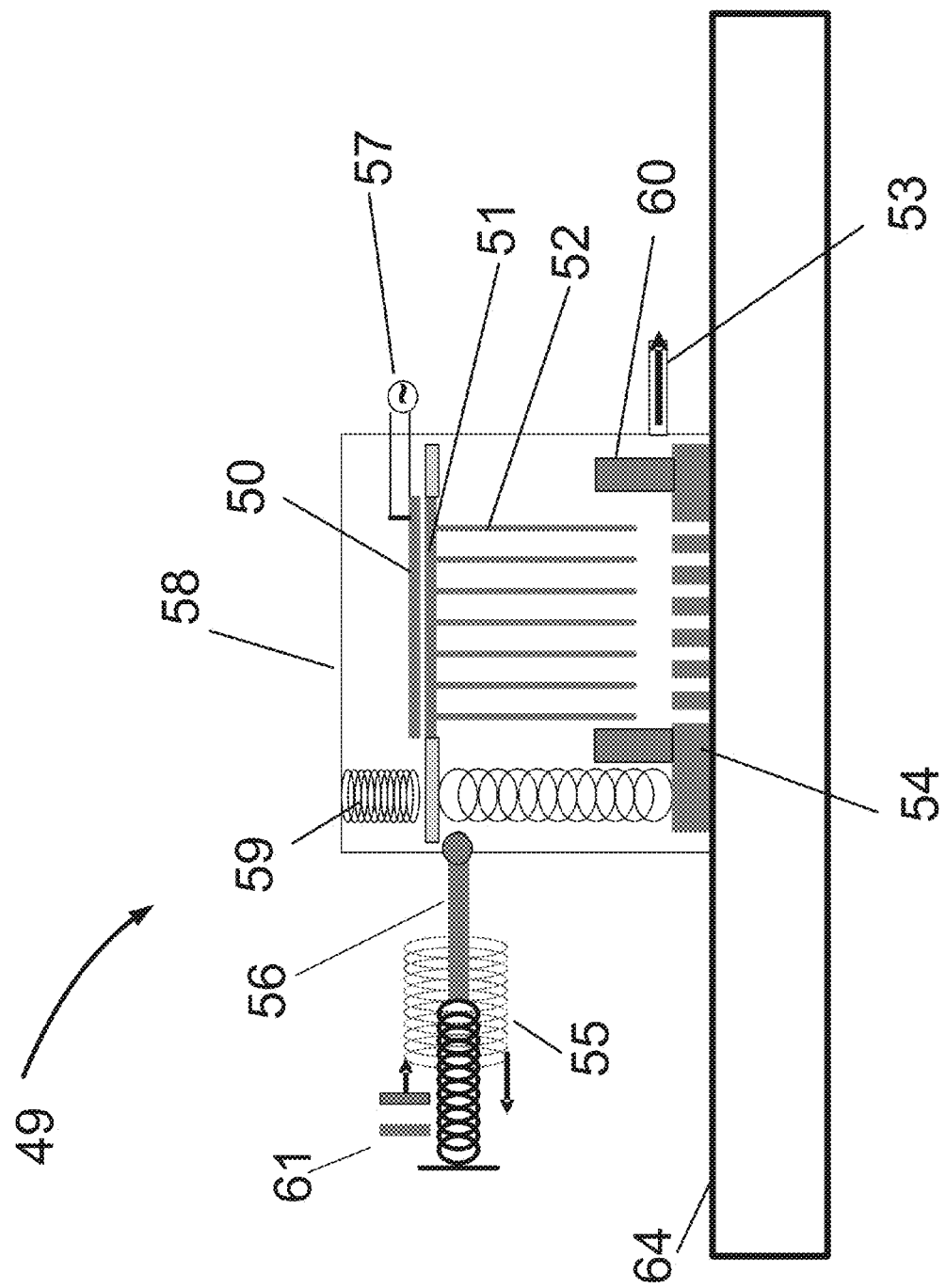
FIG. 5 is a simplified drawing of apparatus according to still another embodiment of the present invention designed for Fraxel skin resurfacing.

Reference is now made to FIG. 5, which is a simplified drawing of apparatus 49 according to still another embodiment of the present invention designed for Fraxel skin resurfacing.

FIG. 5 depicts more detail of an embodiment of the present invention, in use as a skin resurfacing apparatus 49, having an array of 10×10 copper rods 52, as may be used in "Fraxel" skin resurfacing. Various implementation details are provided with reference to the embodiment of FIG. 5. The implementation details are intended as an example, and not meant to be limiting.

A Mica foil heater 50 of a size approximately 10 mm by 10 mm is optionally heated to a temperature in the range from 300 degrees Celsius to 600 degrees Celsius. The heating is powered by an electrical power source 57. In some embodiments the electrical power source 57 may be a battery, and in some embodiments the electrical power source 57 may be a power mains connection, such as a 50/60 Hz line supply.

It is noted that some embodiments of the invention are completely hand-held. In some of the hand-held embodiments, a power supply for the embodiment is a battery packaged within the ablating apparatus.

A copper plate 51 is depicted adjacent to the Mica foil heater 50. In some embodiments of the invention the copper plate 51 may be in contact with the Mica foil heater 51, or optionally at a distance of less than approximately 20 microns from the Mica foil heater 51.

The array of copper rods 52 is optionally integrally bonded to the copper plate 51. The small gap optionally existing between the heater 50 and the plate 51 ensures a rapid enough transfer of heat from the heater 50 to the plate 51, enabling, in the example of FIG. 5, operation of the embodiment at a rate of 1 treatment per second.

The assembly which includes the plate 51 and the rods 52 is heated to approximately 500 degrees Celsius within less than 1 sec.

The thickness of the plate 51 is approximately 50 microns, and the rods are each 5 millimeters long, and 300 by 300 micron wide.

A solenoid and spring assembly 55 with a retaining rod 56 retains the plate and rod assembly 51 52 in position within a housing 58, while one or more springs 59 are loaded. It is noted that the retaining rod 56 may optionally be a magnet, and/or some other rod affected by a magnet, such as an iron rod.

A button and/or switch 61 are actuated by an operator of the skin resurfacing device, at which time the solenoid of the solenoid and spring assembly 55 retracts the retaining rod 56, and the springs 59 accelerate the plate and rod assembly 51 52 toward a skin surface 64.

The springs 59 are optionally selected so as to have a spring constant which ensures an oscillating period of the harmonic oscillator which consists of the springs 59 and the mass of the plate and rod assembly 51 52 to be approximately 100 milliseconds.

A protective plate 54 with holes enables the array of rods 52 to penetrate the protective plate 54 and to vaporize an array of craters in the skin surface 64.

An oscillation amplitude of the rods 52 is designed to be such that the skin is located close to the maximum amplitude, enabling the array of rods 52 to reach the skin at low velocity. An optional spacer 60 optionally ensures a limit to penetration in tissue to a preselected depth of approximately 100 micron. The rod assembly 52 vaporizes an array of craters of substantially precisely 100 micron depth.

The protective plate 54 is optionally produced from a low thermal conduction material, such as a ceramic material. The protective plate 54 also optionally ensures thermal protection of the skin. In some embodiment of the present invention, the protective plate 54 may also be chilled with water or with a thermoelectric chiller.

The oscillatory motion determined by a proper selection of spring constant for the spring or springs 59 and mass of the plate and rods assembly 51 52 ensures a duration of the forward and backward motion in the distal 100 micron section to be approximately 5 milliseconds. This causes a vaporization of the crater array within approximately 5 milliseconds.

On its way back from vaporizing the craters, the plate and rods assembly 51 52 hits the retaining rod 56, and passes beyond the retaining rod 56, reaching its original locked position.

Once back in its original position, the plate 51 is optionally again heated by the foil 50, and is optionally ready to be used on a next treatment site within less than 1 sec. After generation of a crater array on the skin surface, a puff of air is optionally pushed above the plate 54, to remove vapors and/or smoke produced in the vaporization process, and/or to cool the plate 54. The puff of air is optionally provided through a pipe or pipes 53.

In some embodiments of the invention, instead of the spring(s) 59 flicking the rods 52 at the tissue, a solenoid (not shown) flicks the rods to the tissue and retracts the rods 52 from the tissue, optionally by means of a solenoid acting on a magnet connected to the plate and rod assembly 51 52.

Reference is now additionally made to FIGS. 6A-6G, which are simplified drawings of a time sequence of positions of the apparatus 49 of FIG. 5 in operation.

The apparatus 49 is located on the skin surface 64.

FIGS. 6A-6G depicts a time sequence, optionally measured in milliseconds, of events which occur from a moment the plate and rods assembly 51 52 is released, to a moment the plate and rods assembly 51 52 returns to its original position.

On the right side of each one of the FIGS. 6A-6G is a reference to time, in milliseconds, since a beginning of the time sequence.

Each of the FIGS. 6A-6G depicts the components depicted in FIG. 5, using the same reference numbers.

Figure 6A:
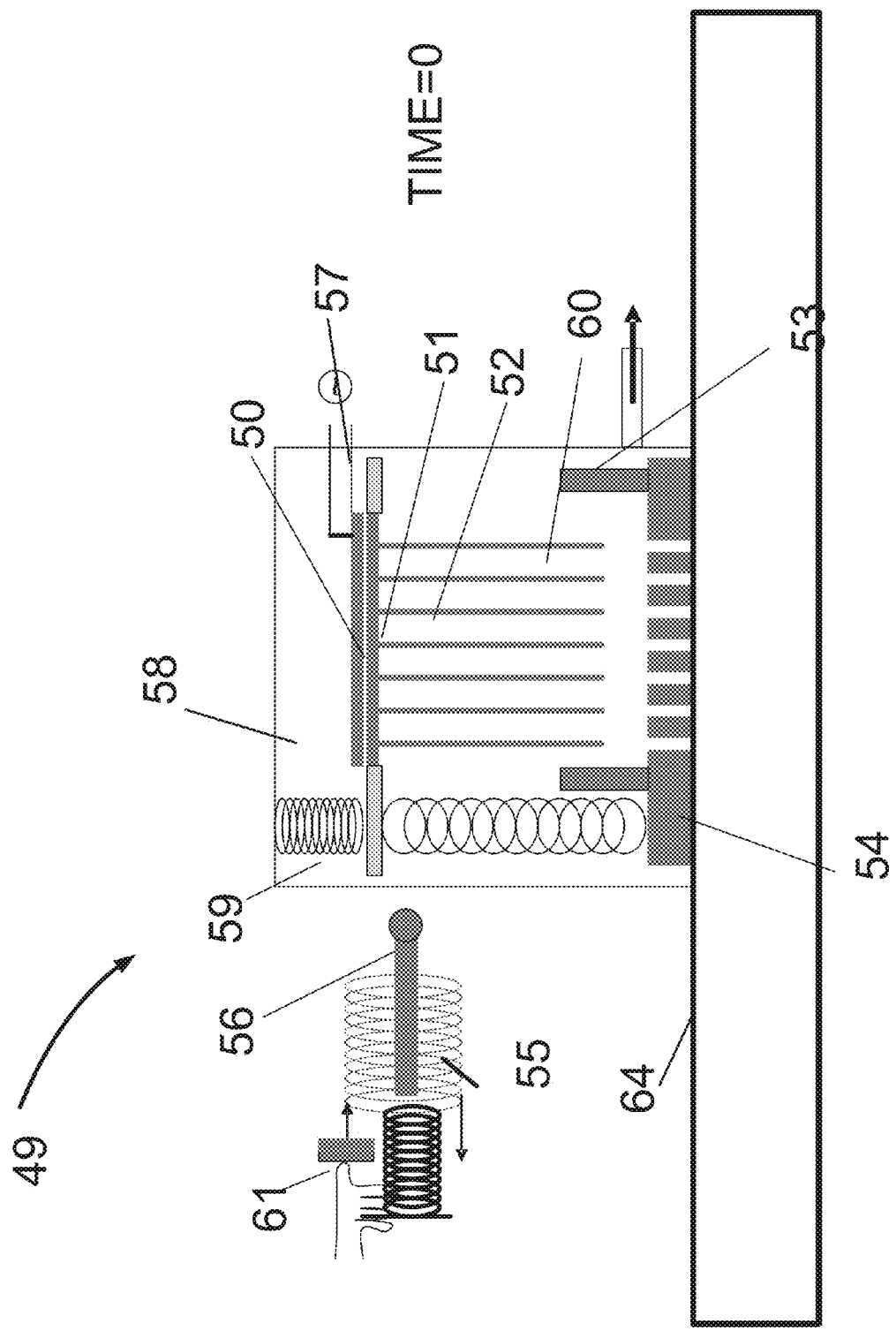
FIGS. 6A-6G are simplified drawings of a time sequence of positions of the apparatus of FIG. 5 in operation.

FIG. 6A depicts the apparatus 49 at time 0, when the solenoid and spring assembly 55 is activated and the plate and rods assembly 51 52 is free to advance toward the skin surface 64.

Figure 6B:
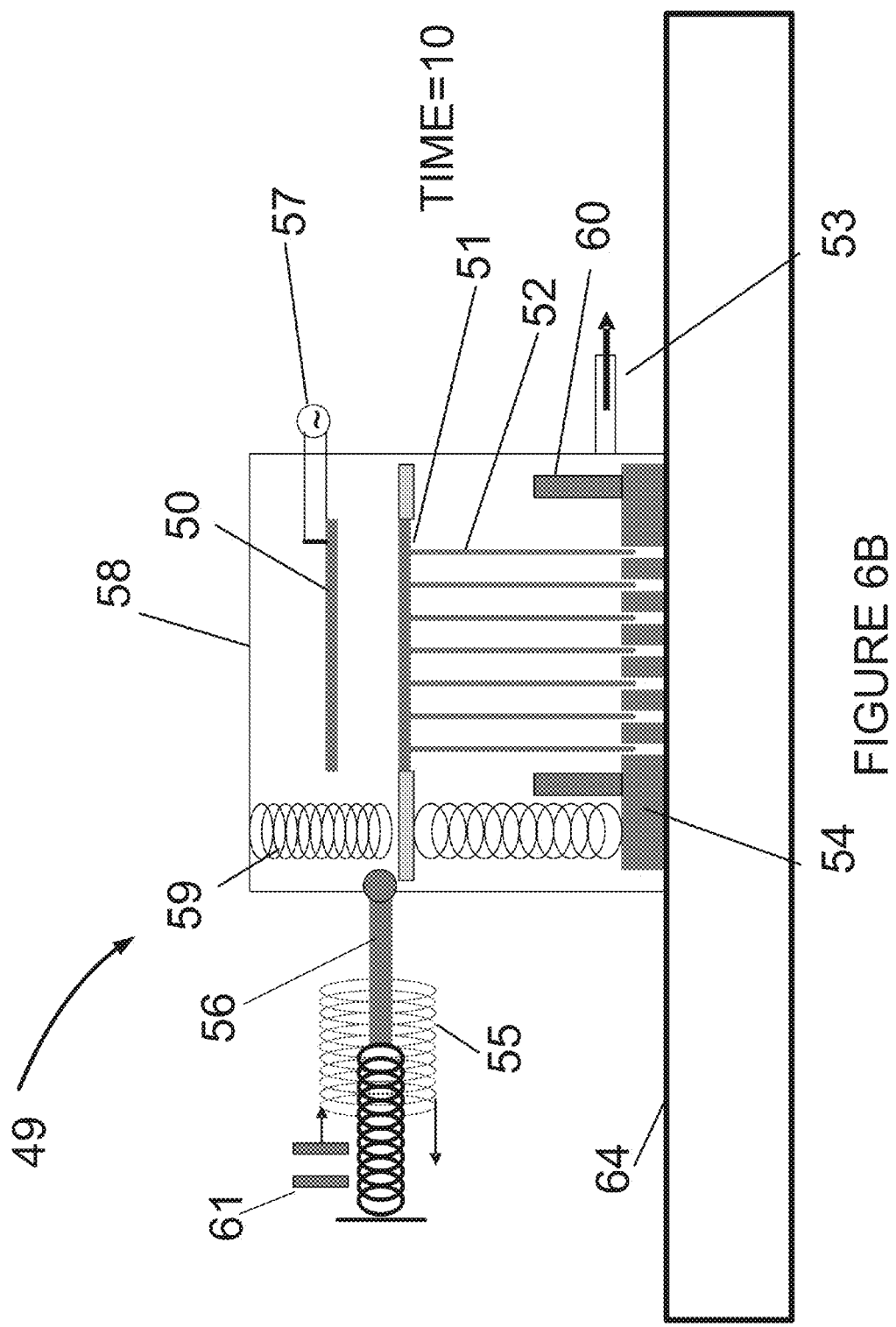

FIG. 6B depicts the apparatus 49 at time 10 milliseconds, when the plate 51 has passed the retaining rod 56. The plate 51 and the rods 52 are in movement toward the skin surface 64.

The retaining rod 56 can return toward its original position, as the plate 51 has passed it. It is noted that the retaining rod 56 may return to its original position at a later point in the operation cycle.

Figure 6C:
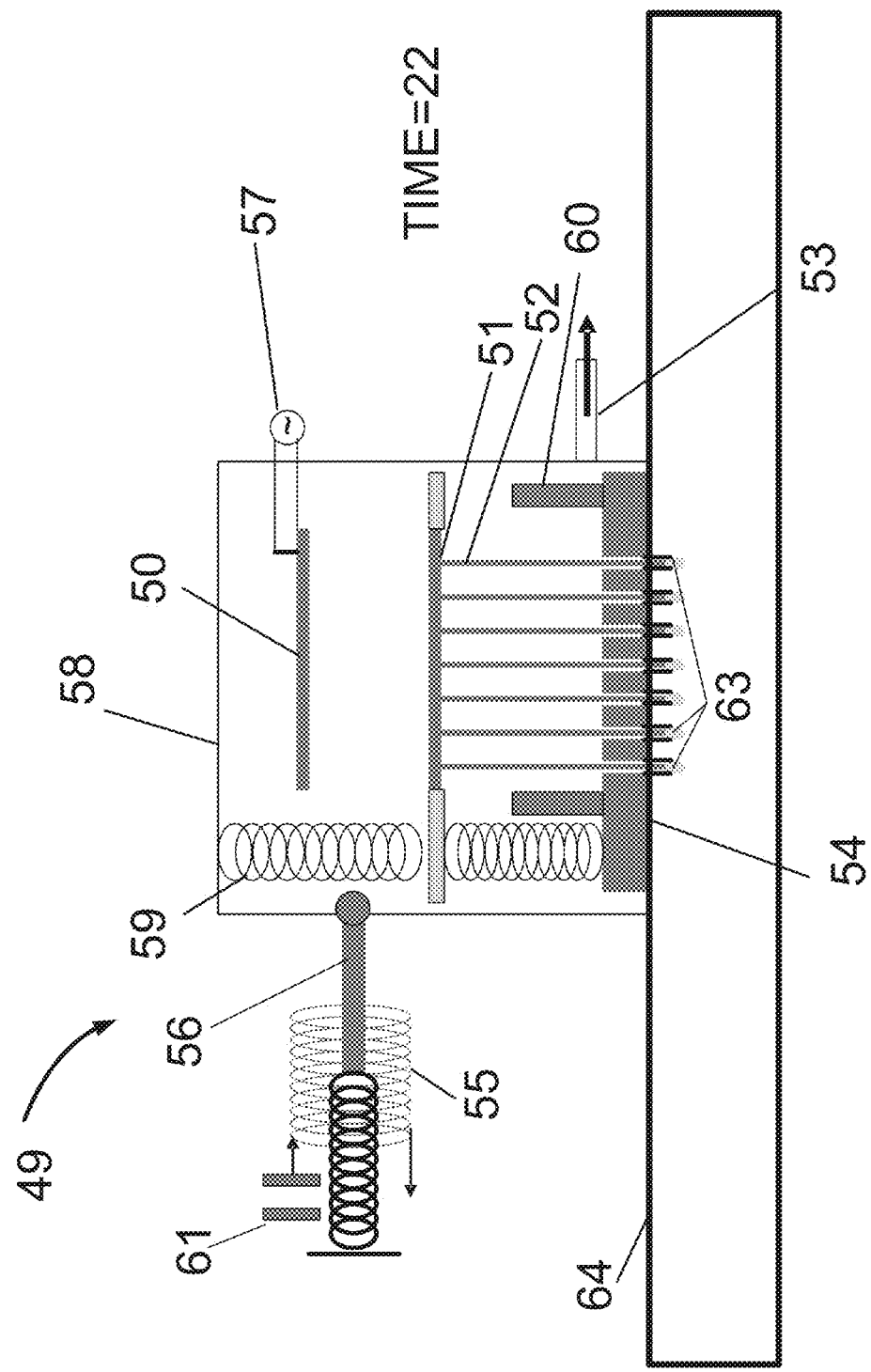

FIG. 6C depicts the apparatus 49 at time 22 milliseconds, when the copper rods 52 start to penetrate the skin surface 64, and start to vaporize craters 63. It is noted that transfer of heat to the skin is limited to a 100 micron zone around the crater walls, and that vapors are substantially trapped, and substantially do not condensate.

Figure 6D:
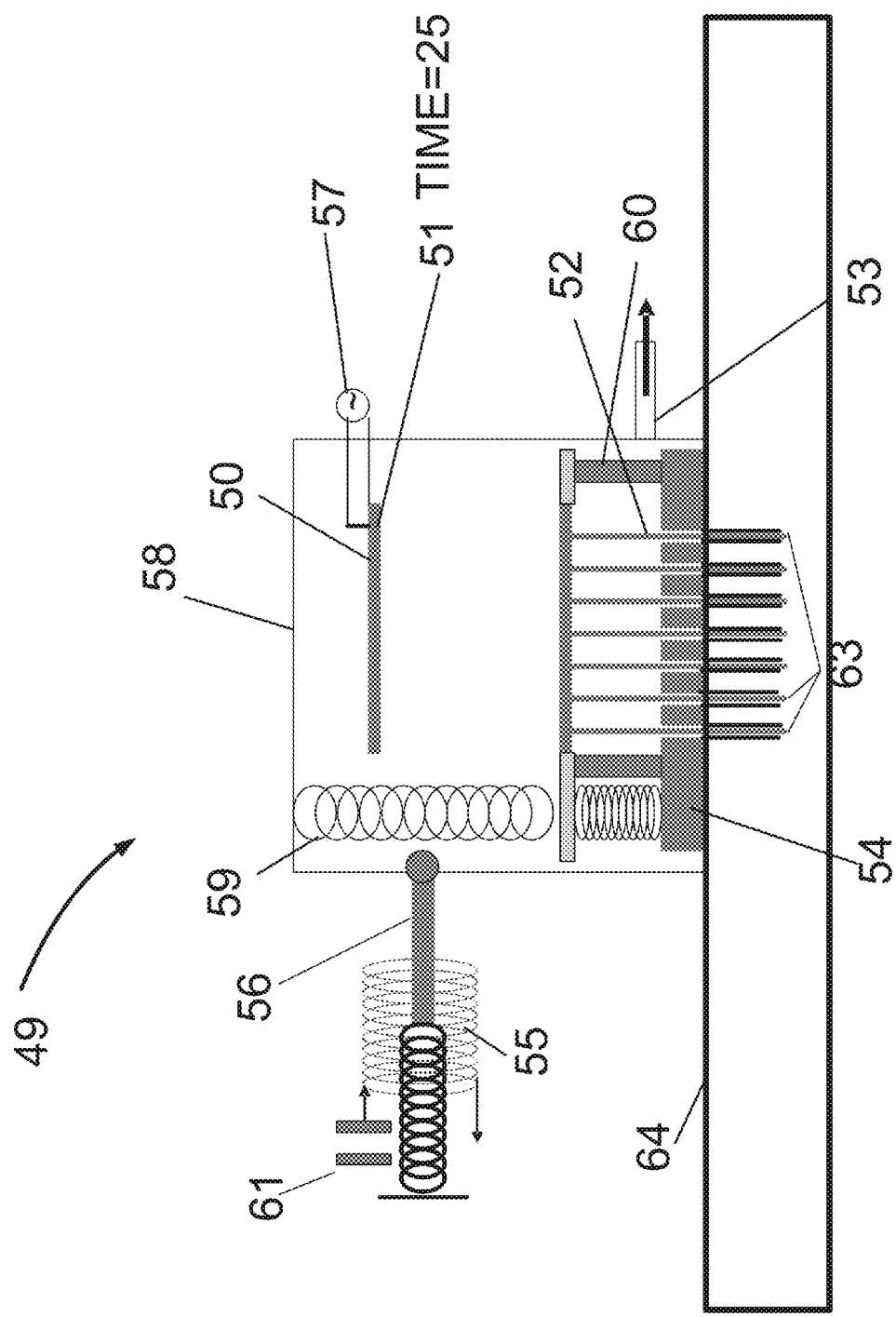

FIG. 6D depicts the apparatus 49 at time 25 milliseconds, when the copper rods 52 reach maximum depth. At this time, approximately 3 milliseconds after initial impact of the copper rods 52 on the skin surface 64, the vapors are still substantially trapped without substantially condensating.

It is noted that in the example of FIGS. 6A-6G the plate 51 impacts on the spacer 60. The impact is calculated to be approximately 10G.

Figure 6E:
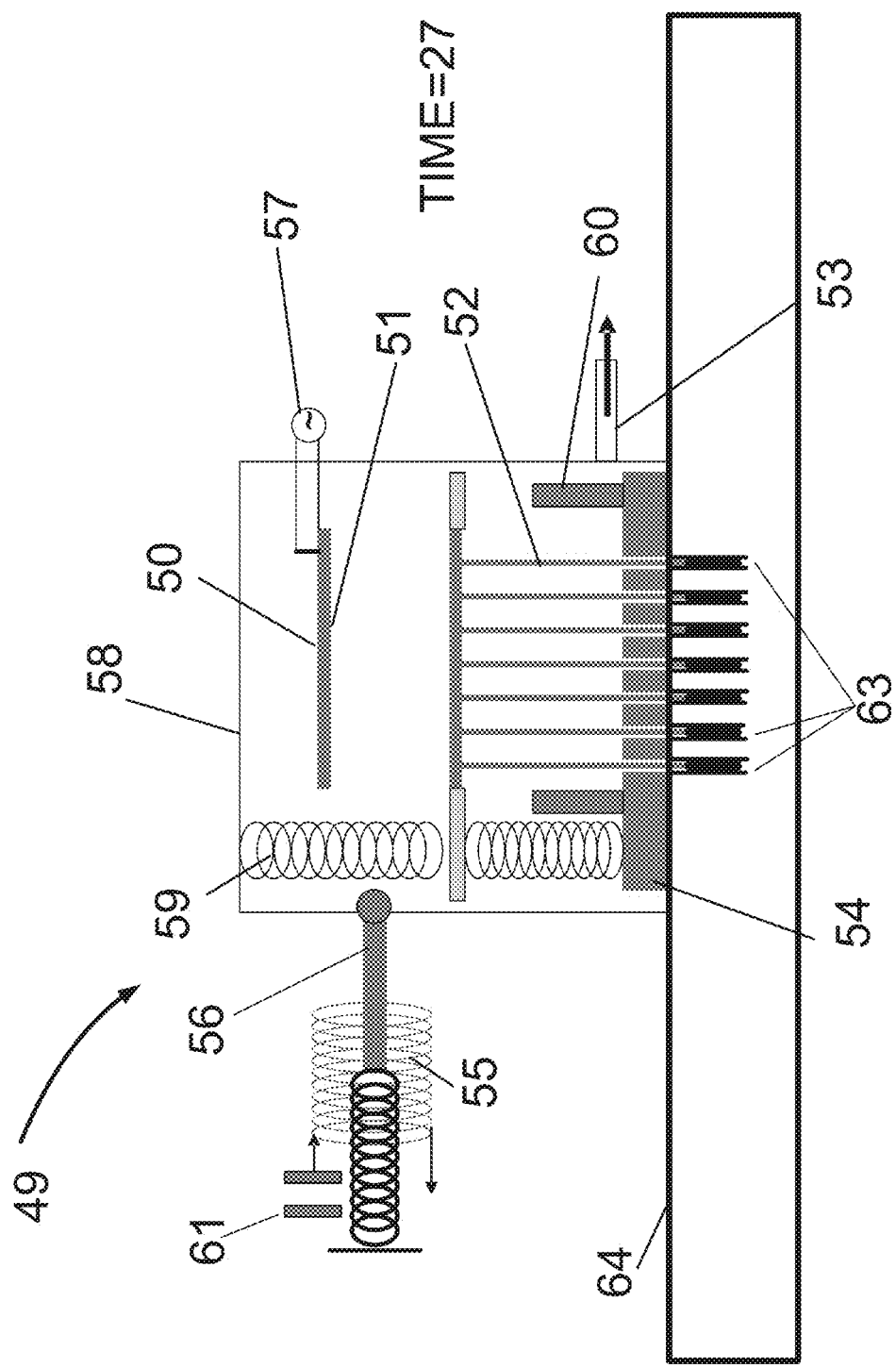

FIG. 6E depicts the apparatus 49 at time 27 milliseconds, when the rods 52 have started their return. It is noted that at this time, approximately 5 milliseconds after initial impact of the copper rods 52 on the skin surface 64, the vapors are still substantially trapped.

Figure 6F:
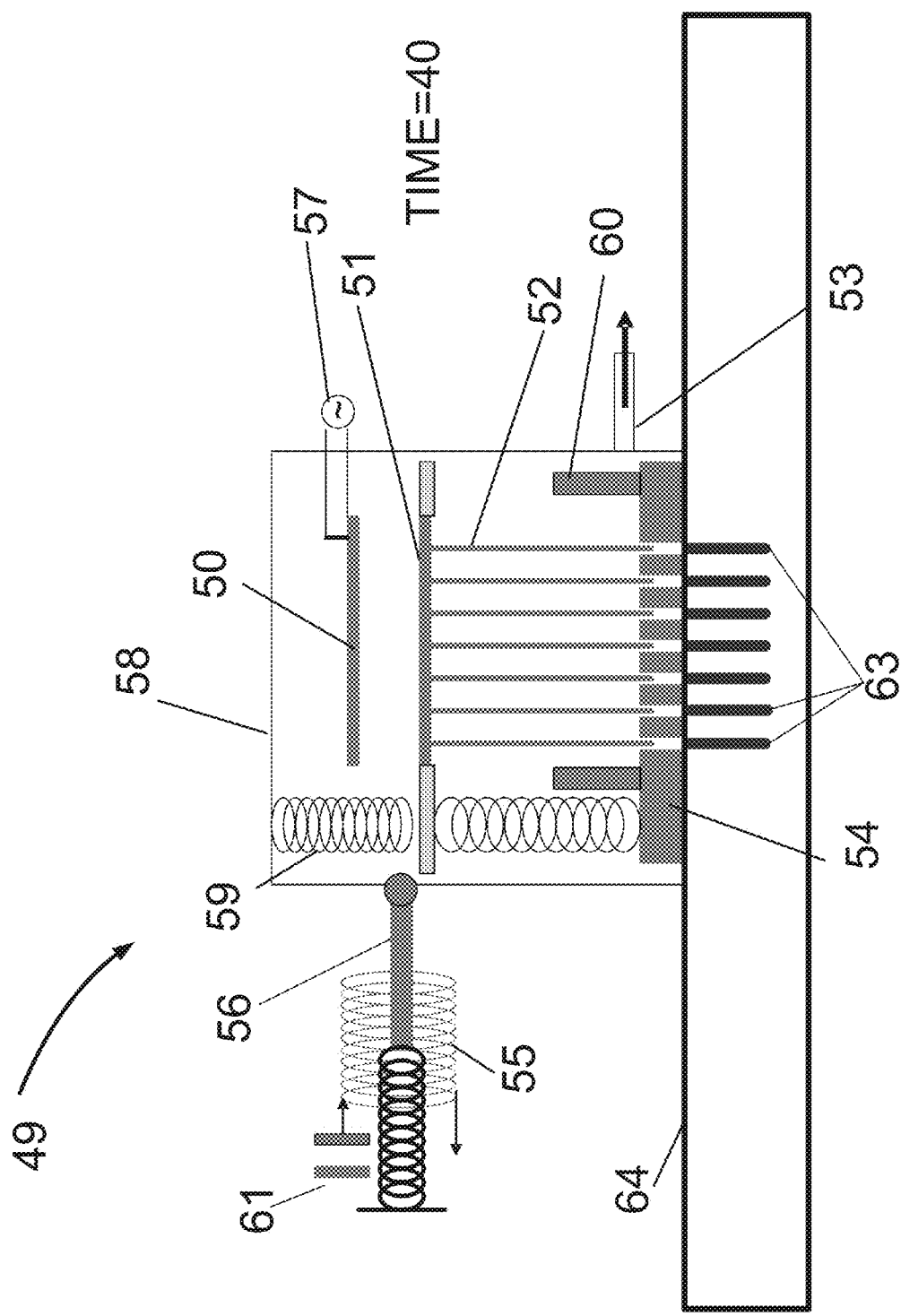

FIG. 6F depicts the apparatus 49 at time 40 milliseconds, when the plate and rods assembly 51 52 starts pushing the retaining rod 56 on its way back to its initial position.

It is noted that at this time the vapors are free to exit the craters 63.

Figure 6G:
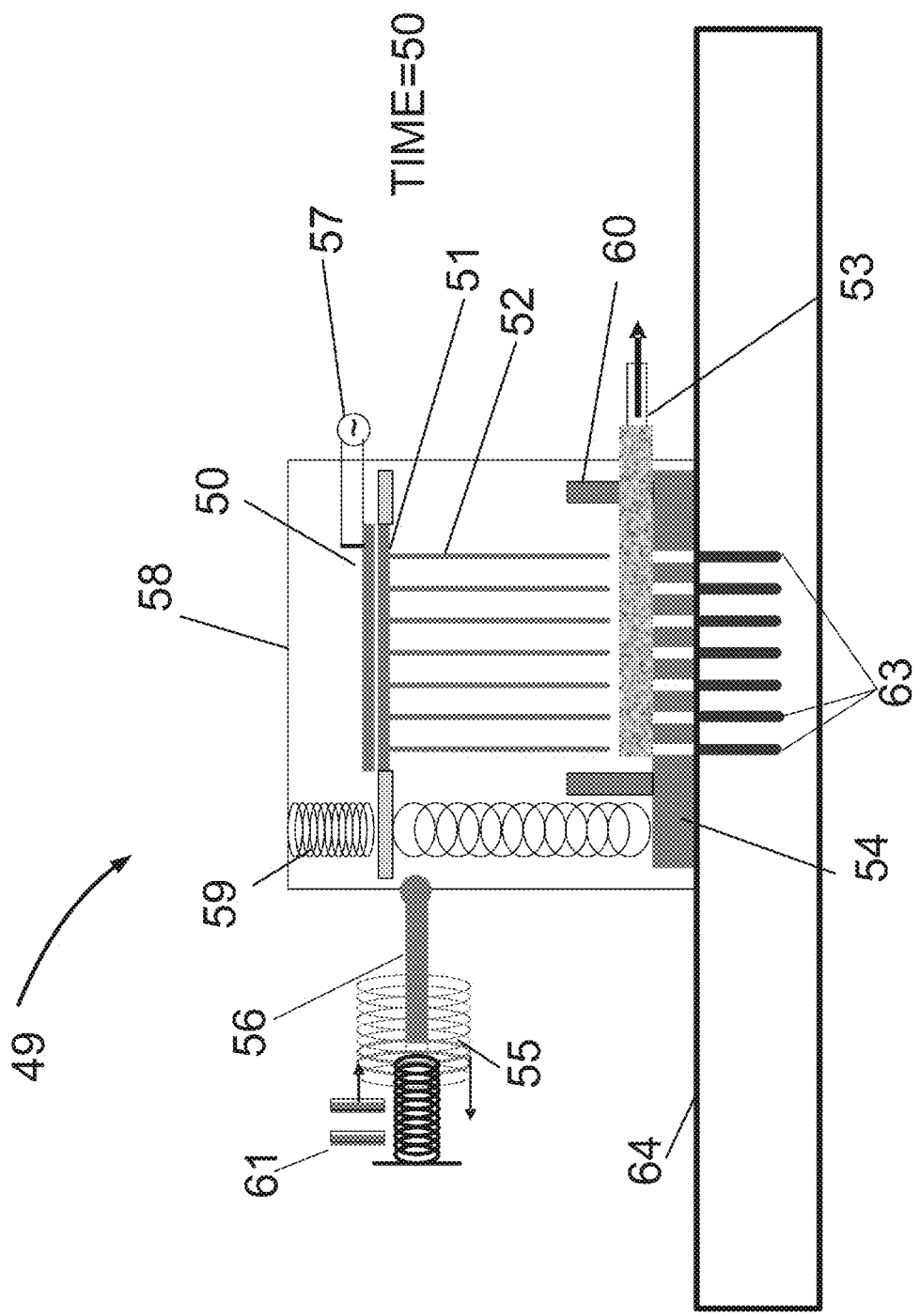

FIG. 6G depicts the apparatus 49 at time 50 milliseconds, at which time the vapors are optionally flushed with a puff of air through the pipe 53.

As mentioned above, in order to ensure delivery of the proper amount of energy for vaporization of craters within a short time duration, the rods are optionally produced from a material with heat conductivity substantially equal to or higher than heat conductivity of copper.

In some embodiment of the present invention, a distal end of the rods is coated with a thin, by way of a non-limiting example, approximately 5 micron, layer of stainless steel, for bio-compatibility.

It is noted that since all the rods have to protrude substantially precisely 100 microns from the protective plate 54 of FIG. 5, the geometric accuracy of the positioning of the spacer 60 over the protective plate 54 should be approximately 50 microns for every 1 centimeter of width of the housing 58. Such geometric accuracy corresponds to approximately 5 milliradians, which is well within a practical range of inexpensive production.

Figure 7:
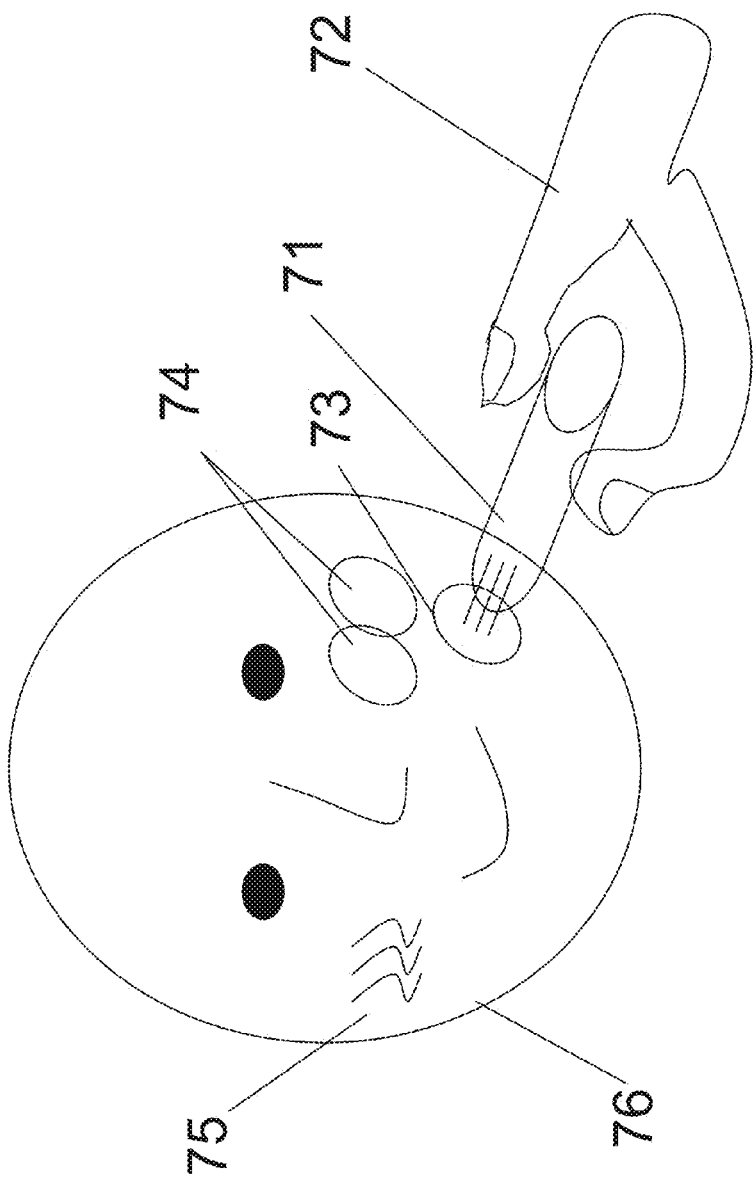
FIG. 7 is a simplified drawing of an apparatus constructed and operative according to an embodiment of the present invention designed for hand-held Fraxel skin resurfacing.

Reference is now made to FIG. 7, which is a simplified drawing of an apparatus 71 constructed and operative according to an embodiment of the present invention designed for hand-held Fraxel skin resurfacing.

FIG. 7 depicts a schematic view of utilization of the hand-held apparatus 71 for skin resurfacing of a face 76. A small apparatus 71 is held by hand 72, and treats sites 73 and 74 for wrinkles 75. Based on the technology used for the present invention, the cost of the apparatus 71 is a small fraction of the cost of a pulsed CO2 laser, while providing similar clinical results.

Figure 8:
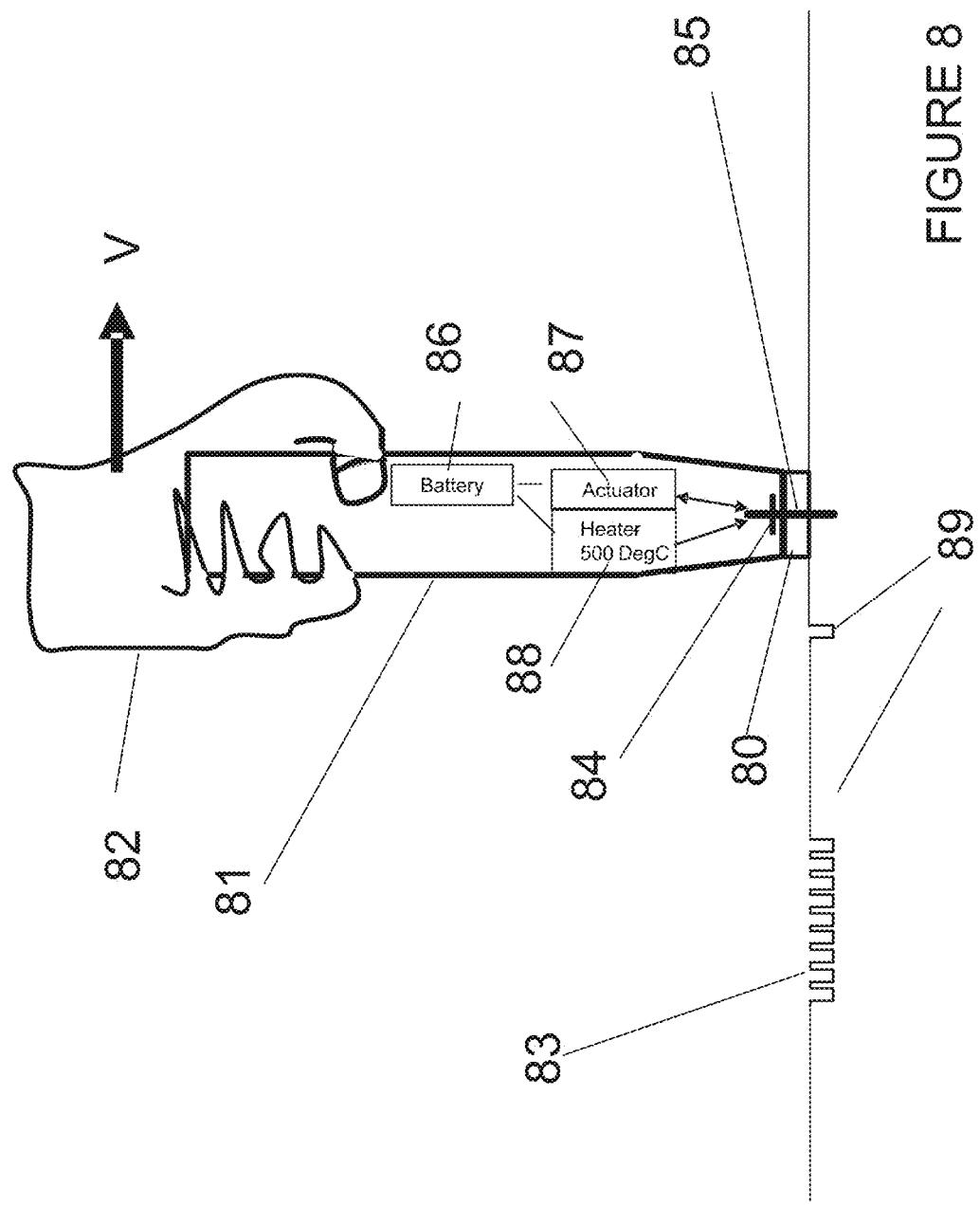
FIG. 8 is a simplified drawing of an apparatus constructed and operative according to an embodiment of the present invention designed for hand-held incision.

Reference is now made to FIG. 8, which is a simplified drawing of an apparatus 81 constructed and operative according to an embodiment of the present invention designed for hand-held incision.

FIG. 8 depicts another embodiment of the present invention, used as a scalpel for making char-free, non-bleeding, high-precision incisions.

The apparatus 81 performs incision substantially equal to incisions made by a tightly focused CO2 laser knife.

The apparatus 81 is optionally driven along an incision course by hand 82.

A copper rod 85 of small diameter, for example of a diameter in the range from 50 microns to 300 microns is heated by a heating element 88 to a temperature in the range of 300 degrees Celsius to 500 degrees Celsius. The rod 85 is optionally vibrated in an up-and-down direction by an actuator 87. The heating element 88 and the actuator 87 are optionally powered by a battery 86, and/or by a connection to a power mains.

The rod 85 protrudes through a hole in an optional protective plate 80, down to a maximum preselected depth of, by way of a non-limiting example, approximately 100 microns.

The apparatus 81 is placed on a surface of tissue 83. Upon operation of the heating element 88 and the actuator 87, the hot rod 85 vaporizes a crater 89 of 100 micron depth. The vibration of the rod 85 is optionally set at a repetition rate of approximately 10 Hz, that is, approximately 100 milliseconds for each round trip of the rod 85. The distal 100 micron end of travel of the rod 85 optionally occurs during approximately 5 milliseconds. A dwell time of the hot rod 85 in the tissue 83 optionally lasts approximately 5 milliseconds, producing in a char-free crater which is similar to craters generated by Ultrapulse and/or Superpulse CO2 lasers.

The high repetition rate of the rod vibration enables a smooth incision line. It is noted that the repetition rate may be higher. By way of a non-limiting example, in cases where a dwell time of the vaporizing rod in the tissue is 5 milliseconds, a repetition rate of approximately 100 Hz, which corresponds to a 10 millisecond vibration, is contemplated. The repetition rate of 100 Hz is twice the dwell time of 5 milliseconds in tissue, allowing 5 milliseconds for the duration of the vaporizing rod outside the tissue.

It is noted that for the embodiment depicted by FIG. 8, the rod 85 may be produced of any metal with heat conductivity which is substantially equal to or higher than the heat conductivity of copper, in order to enable delivery of enough thermal energy, to a depth of up to 100 microns, within a duration of approximately 5 milliseconds.

In order to enable delivery of thermal heat at a repetition rate of, for example, 10 Hz, the length of the copper rod 85 is optionally approximately 2-3 millimeters.

Thermal scalpels produced according to the present invention may be used in skin surgery, such as eyelid surgery, in neurosurgery, for incision of vocal cords, for dentistry and gum surgery, and for laparoscopic surgery, among many other surgical applications.

Figure 9:
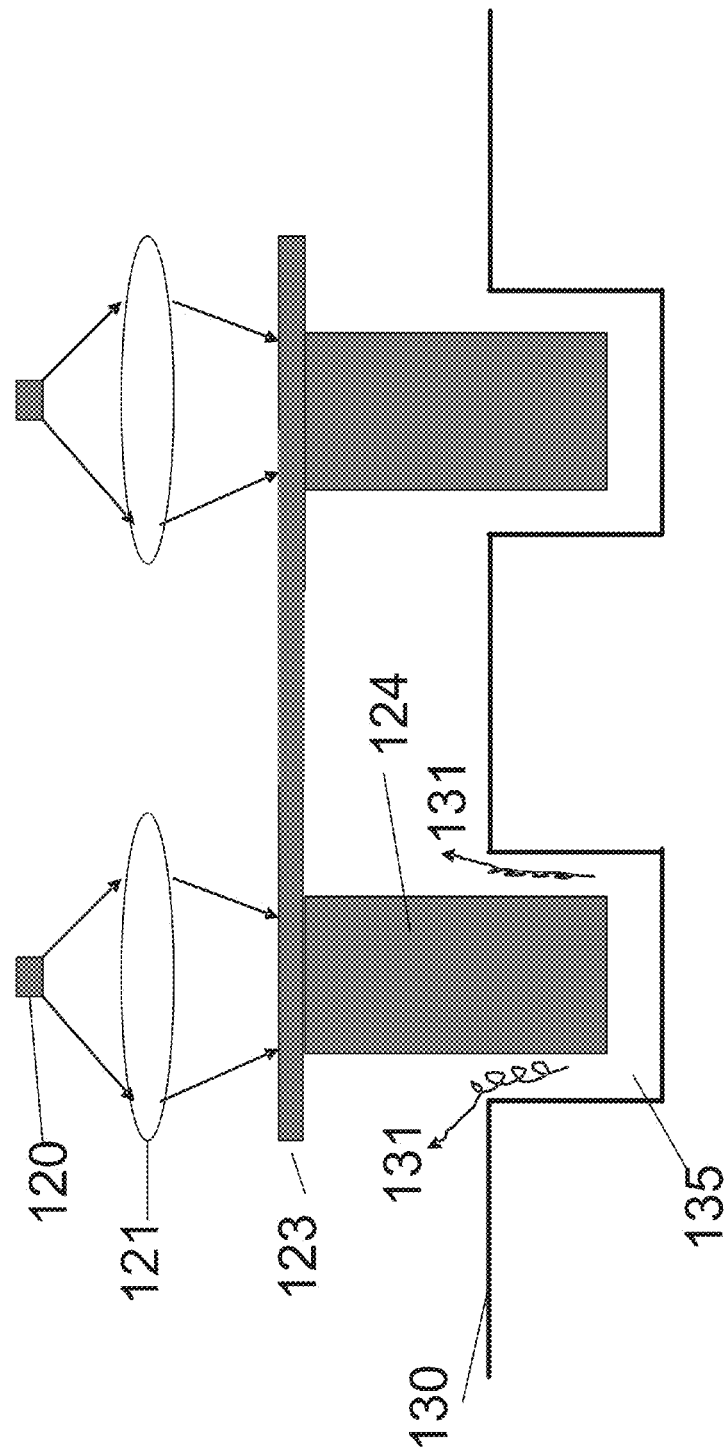
FIG. 9 is a simplified drawing of an embodiment using an optical light source for heating a vaporizing rod.

Reference is now made to FIG. 9, which is a simplified drawing of an embodiment using an optical light source for heating a vaporizing rod.

In the embodiment of FIG. 9, instead of the heating element 50 of FIG. 5, is replaced by an optical heating element.

FIG. 9 depicts light sources 120, with optional lenses 121 which concentrate light on a plate 123. The plate 123 is optionally coated with a black material, such as black gold, and/or black heat-resistant paint, for good light absorption. The plate 123 transfers heat to rods 124, which optionally vaporize tissue 130, producing craters 135, and vapor 131, as described above with reference to FIG. 3.

One advantage of using a light source 120 to heat the plate 123 is a reduction in dimensional accuracy required relative to the dimensional accuracy required in getting the mica foil 50 of FIG. 5 close to the plate 51.

In some embodiments the heating light source is an inexpensive halogen lamp, such as a 50 watt spot light produced by Osram, Germany. In some embodiments the heating light source includes one or more LEDs, optionally arranged as an array of LEDs. In some embodiments the heating light source includes one or more flash-lamps of 500 watts. In some embodiments the heating light source is a short-arc lamp such as produced by Hamamatsu Corporation.

Another advantage of heating the rods 124 with a light source 120 is a possibility to optionally avoid using the heating plate 123 at all, by directly illuminating the rods 124 from the side. With a proper arrangement of a number of rods, it is possible to arrange the rods so that the rods substantially completely block and absorb all light from the light source, similar to lack of horizontal transparency of a forest of trees.

It is noted that by not using the plate 123, the moving mass is reduced.

It is noted that having an option of horizontal lighting provides an additional degree of freedom in designing a tissue vaporizing device.

Figure 10:
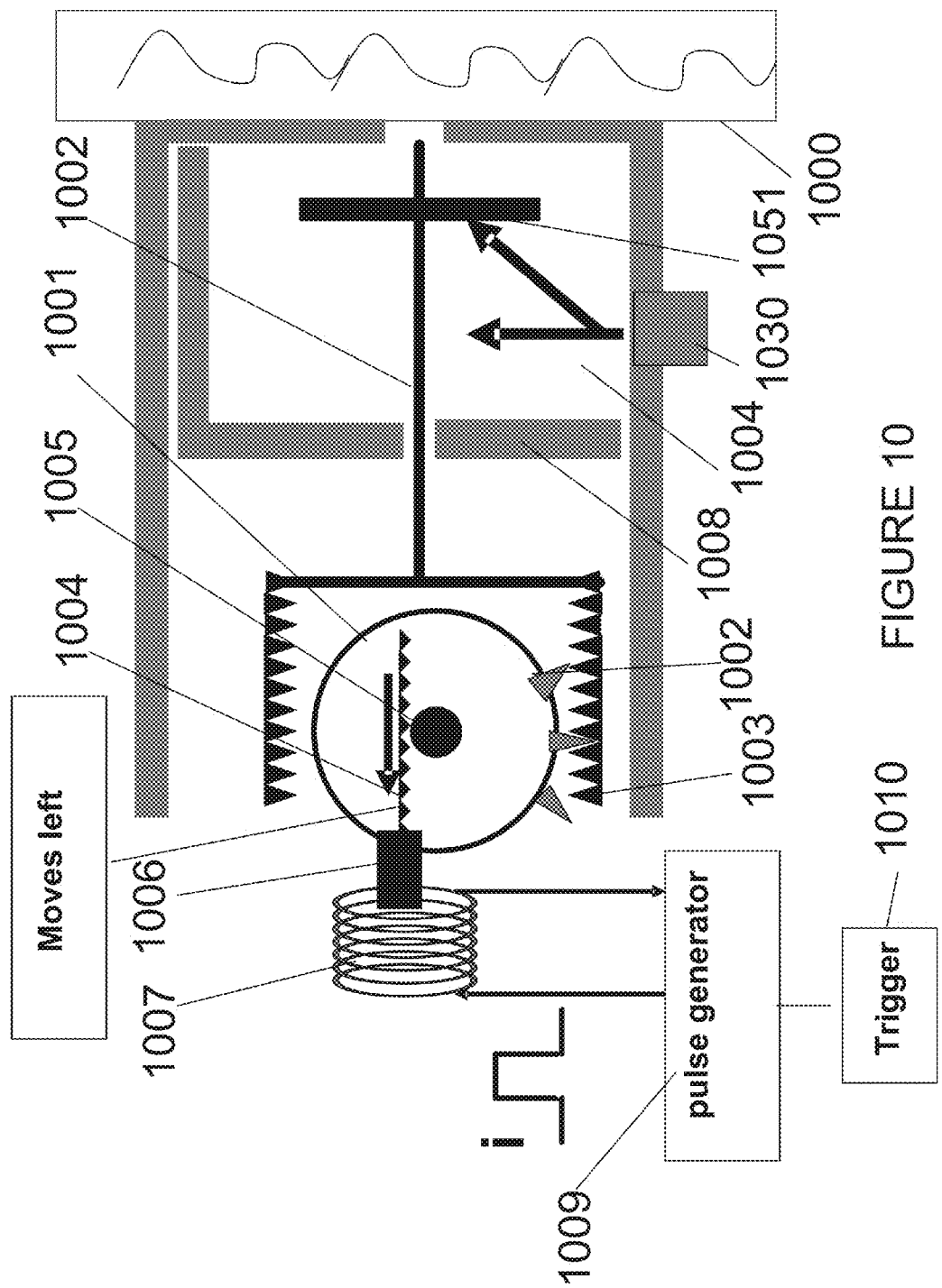
FIG. 10 is a simplified drawing of a mechanism for providing reciprocating movement to one or more vaporizing rods, constructed and operative according to an example embodiment of the present invention.

Reference is now made to FIG. 10, which is a simplified drawing of a mechanism for providing reciprocating movement to one or more vaporizing rods 1002, constructed and operative according to an example embodiment of the present invention.

FIG. 10 depicts a mechanism providing reciprocating movement using a motor, similarly to operation of a needle actuator in a sewing machine.

A solenoid 1007 and an actuating rod 1006 can optionally, upon use of a trigger 1010, be provided with an electric pulse from a pulse generator 1009 and made to move in a linear direction. The actuating rod 1006 includes a row of cogs 1004. When the actuating rod 1006 moves linearly, for example, moves left, the cogs 1004 rotate an axle 1005, which has corresponding cogs (not shown).

The rotating axle 1005 is connected to a cogged wheel 1001, which pushes and pulls on cogs 1003 connected to a vaporizing rod 1002 and a heating plate 1051.

The rod 1002 performs an oscillation movement desired in order to vaporize a crater in tissue 1000.

As described above, the rod 1002 is heated to a temperature which is above the vaporization temperature of tissue, approximately 200 to 500 degrees Celsius.

FIG. 10 also depicts, as an optional alternative embodiment, a light source 1030 which emits light to be absorbed by the rod 1002 and the heating plate 1051, and heat the rod 1002 and the heating plate 1051.

FIG. 10 also depicts as an optional alternative embodiment, a spacer element 1008 used to ensure accurate depth of a vaporized crater.

It is noted that the mechanism of FIG. 10 is suitable for use with a single vaporizing rod, for a multiple vaporizing rod ablator, and for a surgical thermal scalpel.

It is noted that the configuration of FIG. 10 is particularly attractive for the thermal scalpel, since the solenoid 1007 can be repeatedly activated at a repetition rate of, by way of a non-limiting example, 10 Hz, and since the design of FIG. 10 can be miniaturized.

It is noted that in another embodiment, the vaporizing rods is driven using a pneumatic mechanism (not shown), instead of a coil and magnet mechanism.

In another embodiment of the invention, a sensor (not shown) is added to ensure limitation to the depth of penetration in tissue. As a non-limiting example, an optical encoder (not shown) detects an advance of the vaporizing rods, and activates the backward movement once the rods attain a certain distance.

It is noted that in some embodiment of the present invention, the vaporizing rods and/or a protecting plate or a surface which is in contact with tissue are detachable, and/or are disposable, and/or can be sterilized.

It is noted that in some embodiments of the present invention the vaporizing rods may be supplied to users/practitioners separately from other parts of a tissue ablation device.

It is noted that in some embodiments of the present invention the protecting plate may be supplied to users/practitioners separately from other parts of a tissue ablation device.

It is noted that in some embodiments of the present invention the vaporizing rods may be supplied to users/practitioners as a kit with matching protecting plate or protecting plates, separately from other parts of a tissue ablation device.

Figure 11:
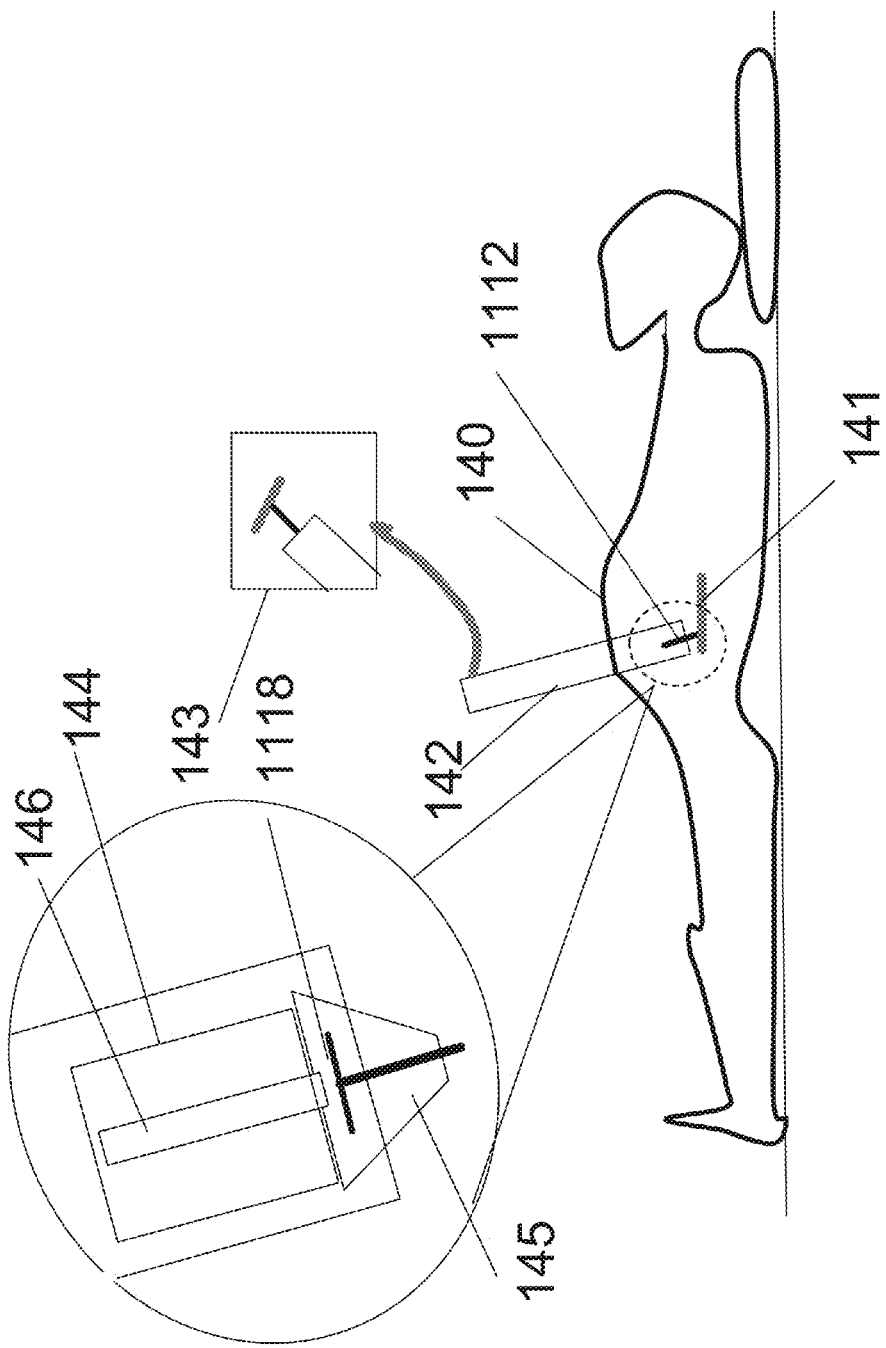
FIG. 11 is a simplified illustration of an example surgical treatment using an embodiment of the current invention delivered via an endoscope.

Reference is now made to FIG. 11, which is a simplified illustration of an example surgical treatment using an embodiment of the current invention delivered via an endoscope.

The non-limiting example of a surgical treatment depicted by FIG. 11 is a delicate and precise non-bleeding incision of a fallopian tube 141, performed with a 300 micron vaporizing rod 1112, which is heated to a temperature of 400 degrees Celsius, and advanced a distance of 100 microns at each step, at a repetition rate of 5 Hz.

The vaporizing rod 1112 is located in a case 144 with a conical end 145, in order to facilitate its advance while being placed on tissue and gradually increasing a depth of an incision. The case 144 and the rod 1112 as well as a rod activating assembly (not shown, similar and optionally smaller than the embodiment depicted in FIG. 8) are located inside a laparoscope 142, which is inserted into an inflated abdomen 140 and optionally viewed on a TV monitor 143.

Since only one rod is used for incision, some embodiments of the invention heat the rod and a heating plate 1118 with a small heating assembly which is inserted into a standard 5 mm laparoscope.

It is noted that a small mechanical mechanism 146 for providing a reciprocating movement to the vaporizing rod can be inserted into the small lumen laparoscope.

It is noted that the embodiment of FIG. 11 can be inserted into any type of endoscope.

It is noted that the embodiment of FIG. 11 can be inserted into a catheter.

Reference is now made to FIG. 12, which is a simplified flow chart illustrating a method of using an embodiment of the present invention as a tissue ablator.

The tissue ablator is powered on (1205).

The vaporizing rod(s) are optionally heated (1210). The vaporizing rod(s) may be heated before use, although they do not have to be heated immediately after powering on, just prior to use for ablating tissue.

The ablator is placed at a treatment site (site of ablation) (1215). The placement at the treatment site may also occur before heating, and also occur before powering on.

Next, an actuator is actuated (1220). For example, a button is pressed, or a switch is switched. The actuator causes an effect such as that of the button and/or switch 61 of FIG. 5, releasing the solenoid and spring assembly 55 of FIG. 5.

If the actuator is actuated, a retaining mechanism such as the solenoid and spring assembly 55 of FIG. 5 releases the vaporizing rod(s) to move forward (1230).

The rod assembly moves forward (1235), and the retaining mechanism optionally returns to its initial position (1240), ready to trap the rod assembly when the rod assembly moves back. It is noted that the retaining mechanism is not required to return to its initial position until the rod assembly moves backward. Thus the returning to the initial position may occur later.

After a short while, the vaporizing rod(s) impinge on tissue, and vaporize the tissue (1245).

The vaporizing rod(s) vaporize the tissue, digging deeper into the tissue, until the rod assembly impacts an optional spacer (1250), and/or is stopped some other way, such as reaching an end of travel possible for the rod assembly.

At this time the rod(s) are at maximum travel (1255).

Vapor from the tissue which the rod(s) vaporized is trapped in the crater(s) (1260).

The rod assembly starts moving back (1265).

The retaining mechanism traps the rod assembly (1270), at which time the rod(s) are back at their start position, and are optionally reheated (1275), ready for another cycle of vaporizing tissue.

At this time, if the actuator is actuated, the vaporizing cycle (1230, 1235, 1240, 1245, 1250, 1255, 1260, 1265, 1270, and 1275) may start again, and if the actuator is not actuated, the cycle stops (1225).

Figure 13:
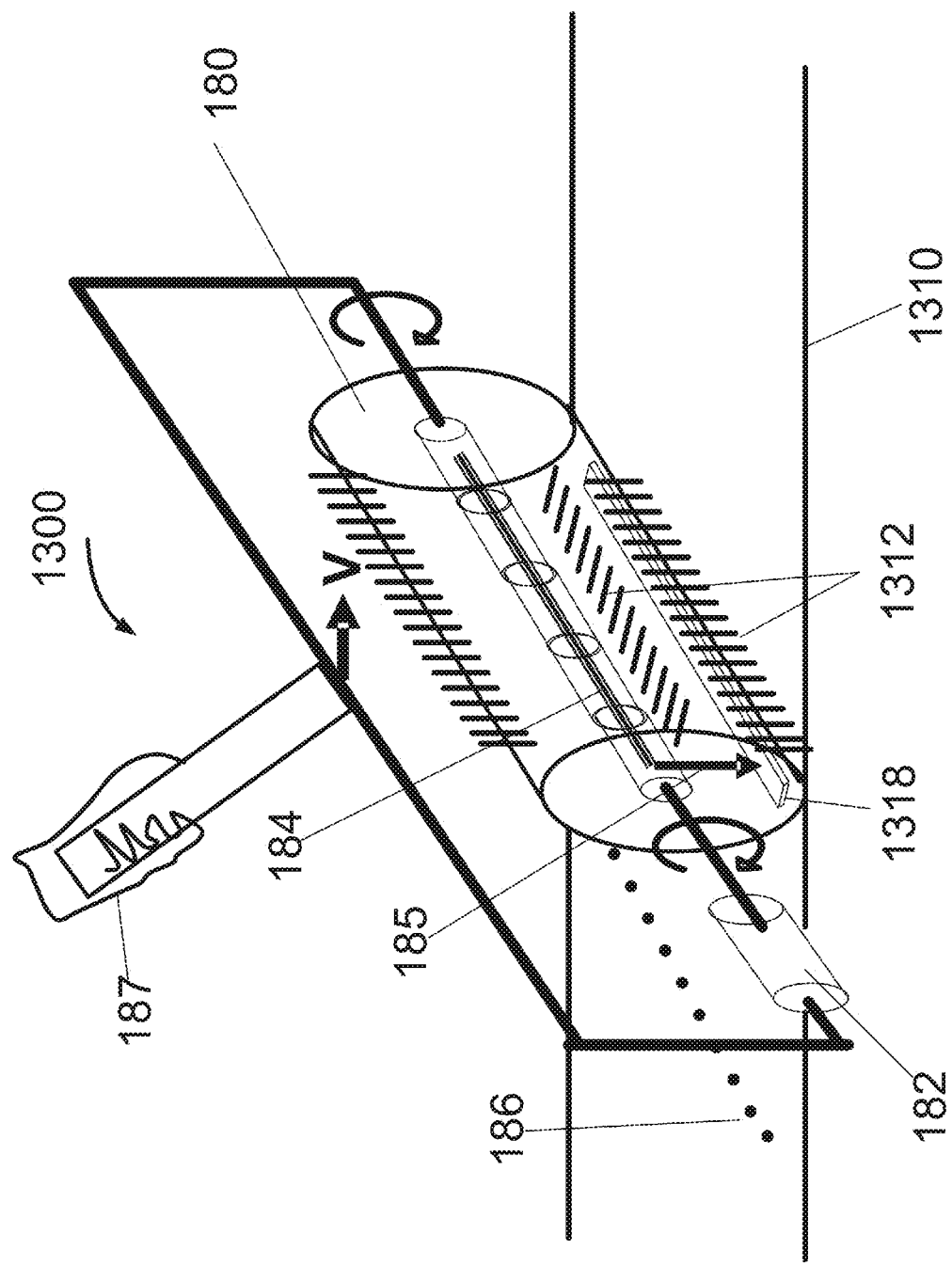
FIG. 13 is a simplified drawing of an apparatus constructed and operative according to yet another embodiment of the present invention, designed for skin resurfacing.

Reference is now made to FIG. 13, which is a simplified drawing of an apparatus 1300 constructed and operative according to yet another embodiment of the present invention, designed for skin resurfacing;

The apparatus 1330 a roller 180 driven at a constant speed V 1301 by a motor 182, over a skin surface 1310, letting a linear array of vaporizing rods 1312 to sequentially vaporize craters 186.

The speed V 1301 is set so as to ensure a dwell time of the vaporizing rods 1312 in the tissue to be approximately 5 milliseconds.

The vaporizing rods 1312 are optionally made from copper, with a diameter of 300 microns, and are optionally coated with an approximately 5 micron stainless steel layer for biocompatibility.

A linear plate 1318 is connected to each linear array of vaporizing rods 1312 and is heated to a temperature of approximately 400 degrees Celsius.

An optional heating element is a linear lamp 184 which emits light 185 focused on each of the linear plates 1318. A width of the linear plates 1318 is approximately 1 mm, and the linear lamp 184 can be an array of LEDs, one or more halogen lamps, or a flashlamp of 500 watts.

The length of the linear array of vaporizing rods 1312 is optionally 10 millimeters, and each array optionally includes ten rods. The distance between tips of the rods in each array is optionally 1 millimeter, in order to generate arrays of craters 186 separated by 1 millimeter. The distance between the craters 186 and dwell time in the tissue dictates the velocity V. For a 1 mm distance and approximately 5 millisecond dwell time, the advance velocity V 1301 is 1 millimeter per 5 milliseconds=20 centimeters per second.

The apparatus 1300 is optionally held by hand 187, and the advancing speed V 1301 is constant and dictated by the motor 182.

In some embodiments of the invention, the roller 180 has a distance between tips of the rods in each array larger than a desired center-to-center spacing for the craters 186. In such embodiments the roller 180 is passed twice, or more, times over the skin surface 1310, allowing a desired offset distance between the craters of one pass and the craters of another pass.

In some other embodiments of the invention, the roller 180 has a distance between tips of the rods in each array larger than a desired center-to-center spacing for the craters 186. In such embodiments two or more rollers 180 are built into the apparatus 1300, such that when passed over the skin surface 1310, two or more sets of craters 186 are produced, at a desired offset distance between the craters of one of the rollers 180, and another (not shown) of the rollers 180.

Figure 14:
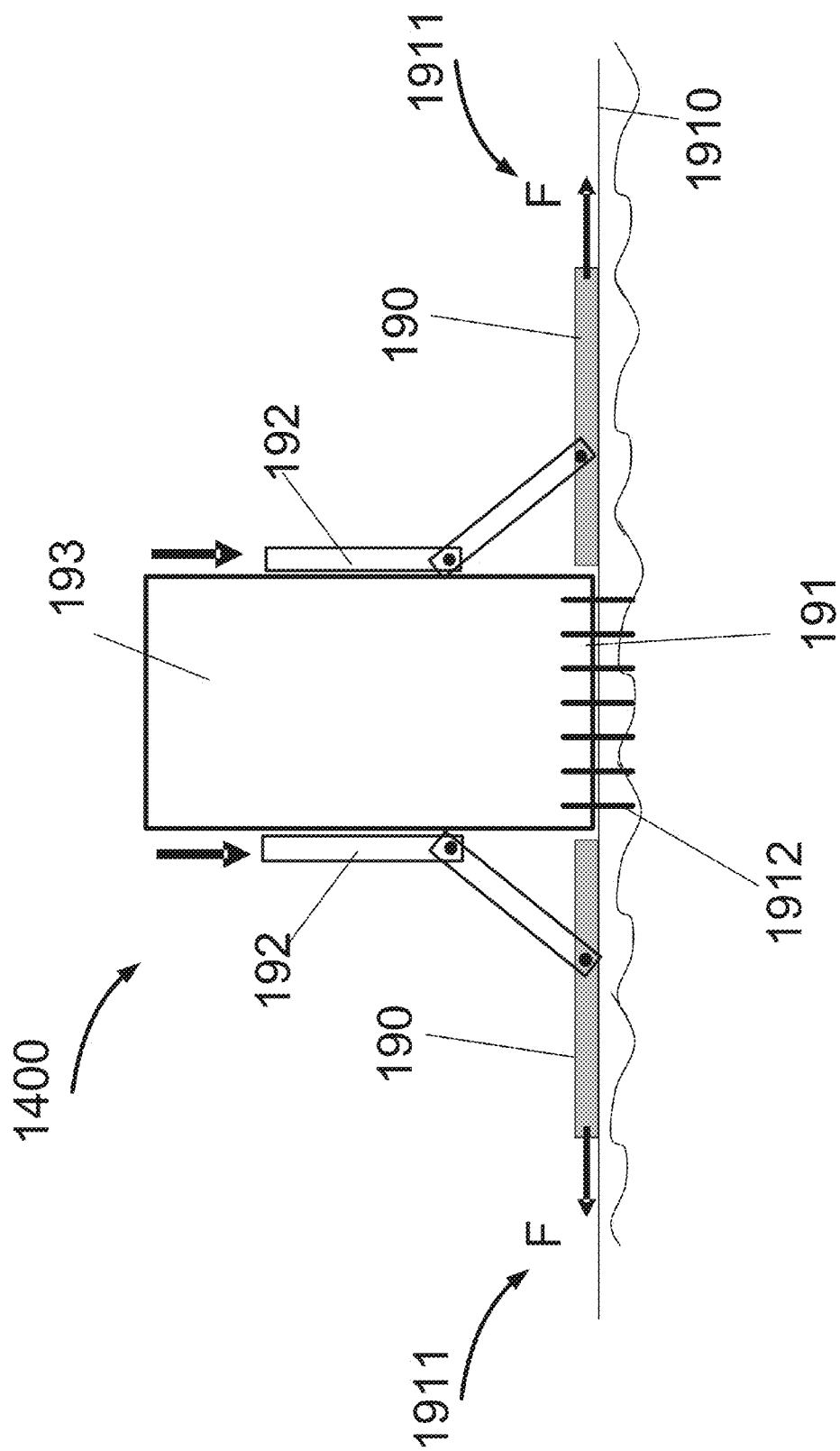
FIG. 14 is a simplified illustration of apparatus useful for stretching tissue while vaporizing some of the tissue, constructed and operative according to yet another embodiment of the present invention.

Reference is now made to FIG. 14, which is a simplified illustration of apparatus 1400 useful for stretching tissue while vaporizing some of the tissue, constructed and operative according to yet another embodiment of the present invention.

The apparatus 1400 optionally stretches tissue, such as skin 1910, while an ablator 193 is pushed against the skin 1910. Stretching the skin 1910 may occasionally be advantageous, when wrinkled skin is treated and a distal surface 191 of the ablator 193 may not be in good contact with all of the skin 1910 along the entire length of the distal surface 191. Not having good contact all along the skin 1910 may result in variations of the crater depths vaporized by vaporizing rods 1912. By stretching the skin 1910, good contact of the distal surface 191 with the skin 1910 is ensured.

An example of a stretching mechanism is an assembly which comprises of elements 192 which are slidingly attached to the ablator 193 and may be pushed downward each time the ablator 193 is placed against the skin 1910. Pressing the element 192 against the skin 1910 induces forces F 1911 on elements 190 which has a rough distal surface and is in contact with the skin 1910, causing the skin 1910 to stretch.

Figure 17:
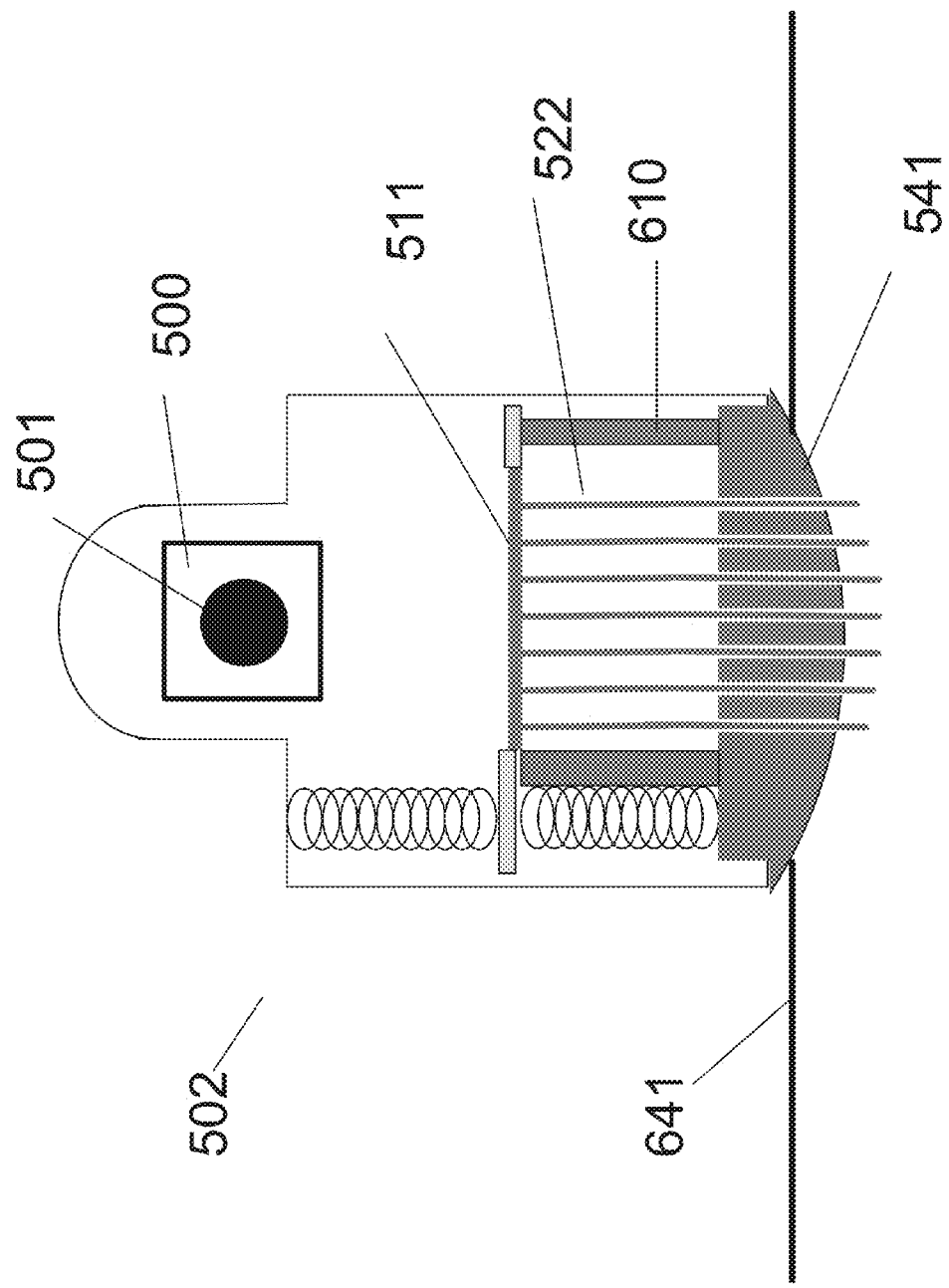
FIG. 17 is a simplified drawing of an apparatus constructed and operative according to yet another embodiment of the present invention, whereby a surface which is in contact with the skin is convex.

Reference is now made to FIG. 17, which is a simplified drawing of an apparatus constructed and operative according to yet another embodiment of the present invention, whereby a surface which is in contact with the skin is convex.

FIG. 17 depicts an apparatus 502 useful for obtaining good contact between distal end 541 and skin surface 641 while vaporizing some of the tissue, constructed and operative according to yet another embodiment of the present invention. A distal element 541 in FIG. 17 optionally has a convex cross section, resulting in both skin stretching and minimal sensitivity to orientation while placing the apparatus 502 on the skin and optionally slightly pressing it against the skin surface. By way of a non-limiting example, the radius of curvature of distal element 541 may be 5-30 mm. Vaporizing rods in FIG. 17 are may optionally be not of equal lengths—they may be longer near the center of distal element 541 and shorter near its edges, resulting in equal protrusion distance from the convex element. This ensures the vaporization of an array of craters with constant selected depth. By way of a non-limiting example, all rods may protrude a distance of 200 micron from the convex surface which is in contact with the skin. FIG. 17 shows vaporizing rods 522 in their tissue vaporizing phase inside the skin, with a plate 511 in its optional position closest to the skin, being stopped by a spacer 610.

FIG. 17 also shows an optional metallic heating element 500, which optionally heats the plate 511 when the rods 522 are optionally in their upper position (farthest from the skin). An optional high power cylindrical heater 501 is optionally inserted inside the element 500, which may be a cubic element made of copper. By way of a non limiting example, the element 500 may be of size 5-30 mm. A non-limiting example of a heating element suitable for use in the apparatus 502 is a 8 mm diameter, 1 inch length, 50 Watt, Watt-FlexR heater cartridge, produced by Dalton Electric Heating Co., MA, USA.

Some non-limiting example applications of clinical procedures using embodiments of tissue ablators constructed and operative according to the current invention are listed below.

Example Application 1

Fraxel skin resurfacing with a 10×10 array of vaporizing rods as described above. The rods are 5 mm long, have a diameter of 300 microns, and are separated by a 1 millimeter center to center distance. The rods are made of copper, coated with a 5 micron stainless steel layer. The rods are heated to a temperature of 400-600 degrees Celsius by a 100 watt per square inch mica HEATFLEX foil, through a copper plate 50 microns thick which is in proximity of 20 micron from the mica foil. The mica heater foil is similar to a mica heater produced by HEATRON, of Kansas, USA. The array of rods is brought against the skin within 25 milliseconds, dwells in the skin for 5-10 milliseconds at a depth of 100-300 microns, and returns to its original position within 25 milliseconds.

An example of a releasing solenoid which may be used in the example application is a tubular solenoid model SDT1327L-2XX produced by NSF Controls, of the UK.

Example Application 2

A hand-held incision ablator device for precise incision of eyelids in eyelid surgery. The incision ablator device uses a single vaporizing rod, similar in dimensions and material to the rods of example application 1.

A distal end of the incision device is conical in shape, with a 600 micron distal diameter. The conical shape allows repeated ablations of ~100 micron depth on a same location, resulting in deeper incisions, such as, by way of a non-limiting example, a 2 millimeter deep incision. The incision device is operated at a repetition rate of 10 Hz. The incision device is capable of incising deeper than 5 millimeters in tissue, without causing bleeding, and with a thermal necrosis of only approximately 100 micron, a feat normally achieved with short pulse $CO_2$ lasers.

Example Application 3

Laparoscopic surgery, for example incision of fallopian tubes, and dissection of adherences. The incision device is generally similar to the incision device of the example application 2, constructed however with a smaller diameter in order to enable insertion into a standard 5 mm laparoscope.

Example Application 4

Neurosurgery.

The rod is utilized to open occlusions which impede ventricular flow. A neuro-endoscope is brought in contact with a ventricle and the rod vaporizes a hole in a membrane which occludes the ventricle. Operation of the incision device is similar to the operation described with reference to example application 2, with the optional aid of a stereotaxis device.

Example Application 5

Ablation of Small Lesions on Vocal Cords.

A single vaporizing rod is optionally operated at a repetition rate of 5 Hz removes nodules and other lesions from vocal cords, without damaging the vocal cord and without causing bleeding. This is particularly important for singers or other people which use their vocal cords professionally. The surgical results are identical to $CO_2$ laser surgery which is currently performed in many ENT surgical suites.

Example Application 6

Colposcopy.

A hand held incision ablator is optionally used for cervical incisions in case of positive PAP smear results which indicate possible presence of HPV. In such cases there is an importance to making a char-free, minimal-thermal-damage incision in cervical surgery, in order to avoid cervical contraction. Such an incision is achieved with an incision device constructed and operating according to the present invention. Results are similar to similar surgical cases which are commonly performed with a pulsed $CO_2$ laser.

Example Application 7

Dentistry and Oral Maxillofacial Surgery.

Embodiments of the present invention for char-free incisions with minimal thermal collateral necrosis and also embodiments for surface vaporization of tissue have applications in dentistry and oral maxillofacial surgery. The embodiments can replace high precision $CO_2$ lasers which are well known to be advantageous both for faster healing and diminished post operative pain. Applications include, by way of some non-limiting examples: gum incision, tissue incision in preparation of dental implants, and ablation of pigmented gums.

Example Application 8

Fractional Skin Rejuvenation Using a High Repetition Rate.

A fractional skin resurfacing unit generally similar to the embodiment described in example 1 is operated at an example speed of between 2 treatment sites/second to 1 treatment site per 3 seconds, or even slower. A treatment speed of 2 treatment sites/second is generally considered as fast. One limit of treatment speed of devices according to the current invention is a time required for heat to diffuse into a distal end of a vaporizing rod following a lifting of the vaporizing rod from tissue immediately after vaporization.

Figure 15:
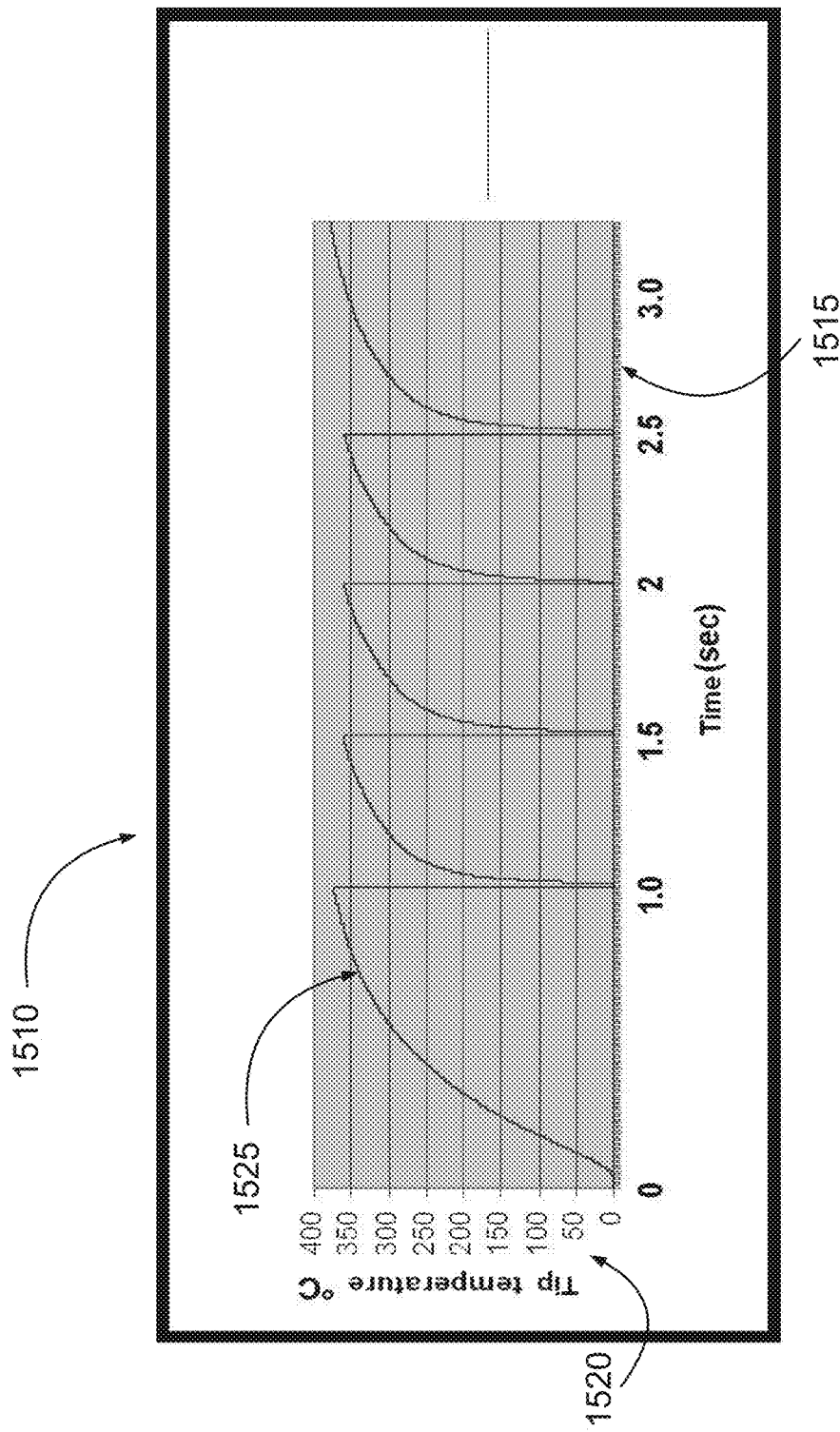
FIG. 15 is a simplified graphical representation of a temperature of a distal end of a vaporizing rod according to a mathematical simulation of an embodiment of the present invention.

Reference is now made to FIG. 15, which is a simplified graphical representation of a temperature of a distal end of a vaporizing rod according to a mathematical simulation of an embodiment of the present invention. FIG. 15 depicts a result of mathematical simulation of a process of heat recharge of the distal end of the vaporizing rod.

FIG. 15 depicts a graph 1510 with an X-axis 1515 depicting time, and a Y-axis 1520 depicting temperature. A line 1525 depicts the temperature of a distal end of a vaporizing rod as a function of time, in an example simulation which employed the following parameters:

A 100 W heater, also produced by the above-mentioned Dalton Electric Heating Co., heats the vaporizing to a maximum temperature of 400 C. The vaporizing rod has a total rod length of 10 mm. The simulation is of heat depletion from the distal 600 microns of the vaporizing rod. Each of the vaporizations of a crater by the rod occurs during a dwell time of 10 milliseconds. The results of the simulation show that a treatment speed of 2 treatment sites/second is achievable.

Example Application 9

Discectomy.

A vaporizing rod is inserted through a catheter into a bulging disk, and vaporizes a hole in the disk.

It is expected that during the life of a patent maturing from this application many relevant surgical lasers will be developed and the scope of the term laser is intended to include all such new technologies a priori.

As used herein the term "approximately" refers to −50% to +100%, that is, measure down to half and up to double.

The terms "comprising", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Reference is now made to the following example, which together with the above descriptions illustrates some embodiments of the invention in a non limiting fashion.

Figure 16A:
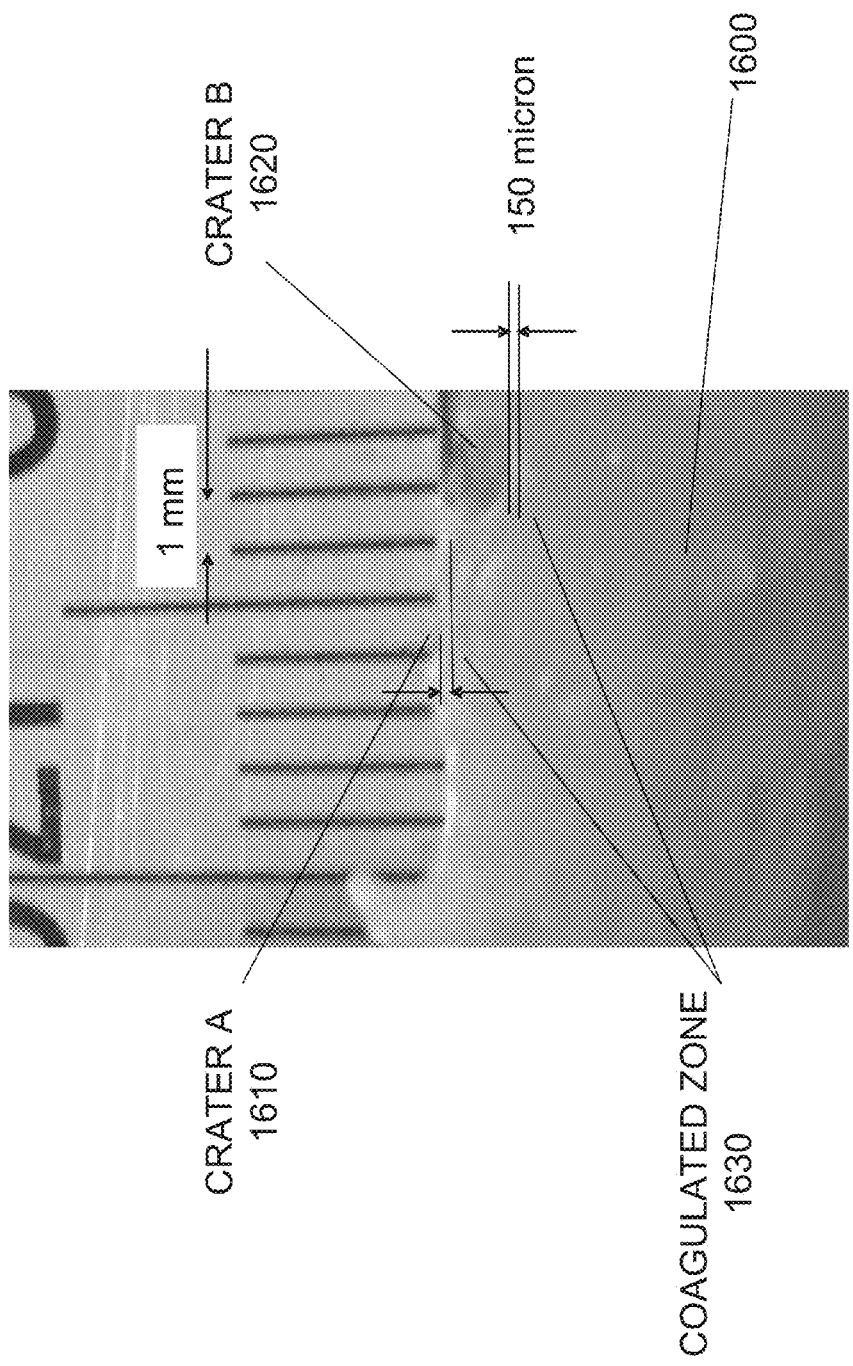
FIG. 16A is a photographic record of two craters produced by a vaporizing rod operative according to physical parameters of embodiments of the present invention.

Reference is now made to FIG. 16A, which is a photographic record of two craters produced by a vaporizing rod operative according to physical parameters of embodiments of the present invention.

FIG. 16A depicts a photograph of two craters on the surface of meat 1600, the craters having been made according to physical parameters of embodiments of the present invention, and a ruler next to the craters for purpose of measurement. The meat 1600 is meat of a chicken.

A metallic vaporizing rod (not shown), 1 millimeter in diameter, was heated to a temperature of approximately 400-600 degrees Celsius, as measured by the color of the metal vaporizing rod. Each time the rod was heated, it was held at a distance of 15 millimeters from the meat 1600, brought in contact with the meat 1600, and retracted from the meat 1600. Each process of touching of the meat 1600 with the hot vaporizing rod lasted a total of 0.1 seconds, and the vaporizing rod was in contact with the meat for approximately 5-10 milliseconds.

FIG. 16A depicts a side view of a first crater A 1610, and it is seen that the depth of the crater A 1610 is approximately 200 microns, with a coagulation zone 1630 around the crater A 1610 of approximately 150 microns.

Similar results are seen with a second crater B 1620, which is more visible as a top view of the second crater B 1620.

It is noted that the same vaporizing rod used for producing the craters when red-hot, could not penetrate the meat when not heated.

Figure 16B:
FIG. 16B is a photographic record of a histological cross section of a crater produced ex-vivo on a skin surface by an array of vaporizing rods operative according to an embodiment of the present invention.

Reference is now made to FIG. 16B, which is a photographic record of a histological cross section of a crater 1630 produced ex-vivo on a skin surface 1635 by an array of vaporizing rods operative according to an embodiment of the present invention.

FIG. 16B depicts a histology of the crater 1630 produced in an ex-vivo test performed on a skin of a domestic white pig.

Figure 16C:
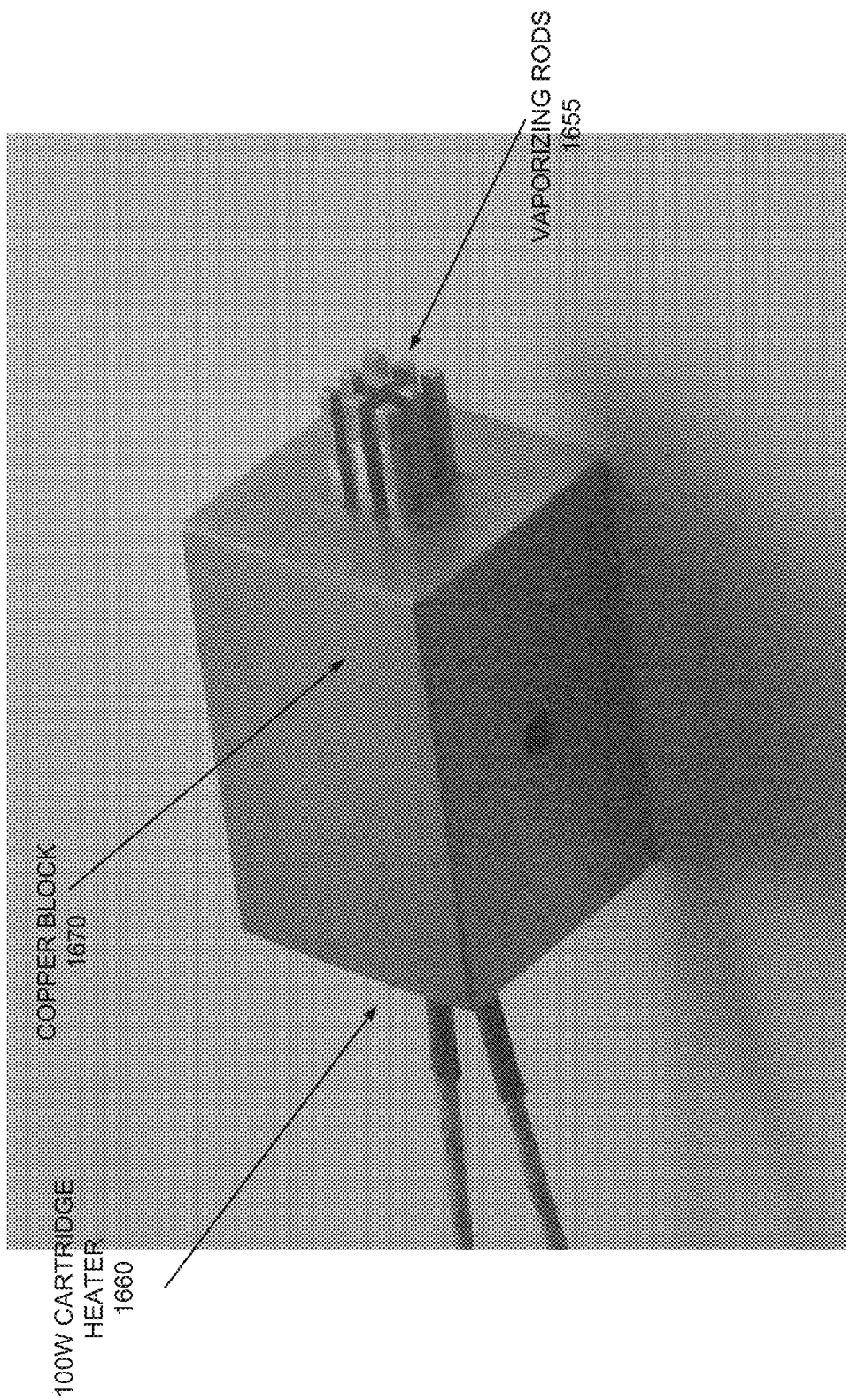
FIG. 16C is a photograph of an array of coated copper rods with a cartridge heater utilized in the embodiment of the present invention which produced a histological cross section depicted in FIG. 16B.

Reference is additionally made to FIG. 16C, which is a photograph of an array of coated copper rods 1655 with a cartridge heater 1660 utilized in the embodiment of the present invention which produced a histological cross section depicted in FIG. 16B FIG. 16C depicts an array of 3×3 vaporizing rods 1655 integrated into a copper block 1670 was heated according to the current invention by a ¼ inch diameter, 1.25 inch length, 100 Watt heating cartridge (produced by Dalton Electric, USA), to a temperature of 400 degrees Centigrade as measured with a thermocouple. The length and width of each of the vaporizing rods 1655 were 10 mm and 1.5 mm respectively. The copper block 1670 was coated with a 1 micron thick layer of Rhodium (not shown) for biocompatibility. A separation between the vaporizing rods was 1 mm.

In order to produce the results depicted in FIG. 16B the array of vaporizing rods was brought in contact with the skin thirty times, at thirty different treatment sites, at a repetition rate of approximately 1 contact every half a second, for a dwell time duration of 5-10 milliseconds. Vaporized craters of approximately 200 micron depth, with collateral damaged zone 1640 of a depth of approximately 250 microns were produced. The collateral damage zone 1640 is partly a coagulated layer with a depth of approximately 150 microns, and partly an additional thermal diffusion layer of 100 micron depth where vital cells can be found.

It is noted, that by changing a length of the vaporizing rods in a range of approximately 5-20 mm, and a duration of the oscillation in the bringing into contact mechanism described above to approximately 10-200 milliseconds, it is possible to practically cover a wide range of clinical parameters, namely changing a vaporization depth of 10 microns to 500 microns, a vaporization dwell time of approximately 0.1 milliseconds to 10 milliseconds, and a collateral thermal damage of 20 microns to approximately 300 microns.

It is noted that an optimal selection of parameters may also depend on a relative density of the vaporizing rods in the array of vaporizing, which may be defined as a ratio of a total distal end area to a total area of gaps between the vaporizing rods. In some embodiments the ratio may vary between 5% and 80%. A preferred optimal density may vary between 10% and 50%.

It is noted that a combination of vaporizing rod temperature, vaporization depth, collateral damage depth, rod width, and rod density affects both remodeling efficacy without scar as well as healing time. According to the current invention, these parameters are controllable.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:
1. A device for skin treatment comprising:
a heated vaporizing element comprising:
   a hollow titanium element with a closed tip; and
   a heating element within the hollow titanium element; and
   a mechanism configured to advance the heated vaporizing element into live skin and retract the heated vaporizing element from the live skin, said heated vaporizing element configured to produce a hole in the live skin, wherein the heating element is arranged to be heated to a temperature in a range of 200 to 600 degrees Celsius before said heated vaporizing element is advanced.

2. The device of claim 1 in which an external surface of the heated vaporizing element comprises a biocompatible coating.

3. The device of claim 1 further comprising the hollow titanium element being filled with a heating element comprising heat conducting material.

4. The device of claim 1 in which the heating element comprises copper.

5. The device of claim 1 in which the heated vaporizing element is composed entirely of titanium.

6. The device of claim 1 in which the heated vaporizing element comprises a plurality of tips.

7. The device of claim 1 in which the heated vaporizing element comprises a shape with a cross section selected from a group consisting of:
- a solid circle;
- a solid rectangle;
- a hollow circle;
- a hollow rectangle;
- a straight line;
- a curve; and
- a wavy line.

8. The device of claim 1 wherein the heating element further comprises a component for heating the heating element.

9. The device of claim 8 in which the heating element comprises exothermic chemical reactants.

10. The device of claim 8 in which the component for heating the heating element comprises an electrical resistor.

11. The device of claim 1 in which an inner dimension of the hollow titanium element is in a range of 100-1600 microns.

12. The device of claim 1 in which an outer dimension of the hollow titanium element is in a range of 150-1800 microns.

13. The device of claim 1 in which a wall thickness of the hollow titanium element is in a range of 50-200 microns.

14. The device of claim 1 in which the heating element comprises a material for heating by an exothermic reaction.

15. The device of claim 1 wherein the device further comprises a component for heating the heating element which is external to the heating element.

16. The device of claim 15 in which the component for heating the heating element comprises an electrical resistor.

17. The device of claim 1 in which the hollow titanium element with a closed tip is composed entirely of titanium with a closed titanium tip.

18. A method of evaporating skin comprising:
- heating a vaporizing element to a temperature in a range of 200 to 600 degrees Celsius;
- advancing the heated vaporizing element into live skin and retracting the heated vaporizing element from the live skin, said heated vaporizing element producing a hole in the live skin, the vaporizing element comprising:
  - a hollow titanium element with a closed tip; and
  - a heating element within the hollow titanium element;
- wherein the advancing the heated vaporizing element is to a depth which is smaller or equal to a papillary dermis depth within the tissue; and
- the retracting the heated vaporizing element from the tissue is after a short duration, the short duration being short enough to prevent collateral damage further than 150 microns from the hole vaporized in the live skin.

* * * * *